United States Patent
Pourmand et al.

(10) Patent No.: US 10,345,260 B2
(45) Date of Patent: Jul. 9, 2019

(54) NANOPORE DEVICE FOR REVERSIBLE ION AND MOLECULE SENSING OR MIGRATION

(71) Applicant: The Regents of the University of California, Oakland, CA (US)

(72) Inventors: Nader Pourmand, Scotts Valley, CA (US); Boaz Vilozny, Santa Cruz, CA (US); Paolo Actis, London (GB); R. Adam Seger, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 226 days.

(21) Appl. No.: 14/641,064

(22) Filed: Mar. 6, 2015

(65) Prior Publication Data

US 2015/0177189 A1 Jun. 25, 2015

Related U.S. Application Data

(62) Division of application No. 13/411,221, filed on Mar. 2, 2012, now Pat. No. 8,980,073.

(Continued)

(51) Int. Cl.
*G01N 27/447* (2006.01)
*B01L 3/02* (2006.01)
(Continued)

(52) U.S. Cl.
CPC ........ *G01N 27/44791* (2013.01); *B01L 3/021* (2013.01); *B01L 3/50273* (2013.01);
(Continued)

(58) Field of Classification Search
CPC .......... G01N 27/447; G01N 27/44791; G01N 33/48721; C25B 7/00; G01Q 60/44
See application file for complete search history.

(56) References Cited

U.S. PATENT DOCUMENTS

| 4,384,075 A | 5/1983 | Grossi et al. |
| 7,655,791 B2 | 2/2010 | Makarov et al. |

(Continued)

FOREIGN PATENT DOCUMENTS

WO   2006/000064 A2   1/2006

OTHER PUBLICATIONS

Powell et al (Nature Nanotechnology, vol. 3, 2008, pp. 51-57, http://www.nature.com/nnano/journal/v3/n1/pdf/nnano.2007.420.pdf).*

(Continued)

*Primary Examiner* — Alexander W Keeling
(74) *Attorney, Agent, or Firm* — Shweta Chandra; Bozicevic, Field & Francis LLP

(57) ABSTRACT

Disclosed are methods and devices for detection of ion migration and binding, utilizing a nanopipette adapted for use in an electrochemical sensing circuit. The nanopipette may be functionalized on its interior bore with metal chelators for binding and sensing metal ions or other specific binding molecules such as boronic acid for binding and sensing glucose. Such a functionalized nanopipette is comprised in an electrical sensor that detects when the nanopipette selectively and reversibly binds ions or small molecules. Also disclosed is a nanoreactor, comprising a nanopipette, for controlling precipitation in aqueous solutions by voltage-directed ion migration, wherein ions may be directed out of the interior bore by a repulsing charge in the bore.

19 Claims, 22 Drawing Sheets

Related U.S. Application Data

(60) Provisional application No. 61/449,379, filed on Mar. 4, 2011.

(51) Int. Cl.
  *B01L 3/00* (2006.01)
  *B82Y 35/00* (2011.01)
  *G01N 33/487* (2006.01)
  *G01Q 60/44* (2010.01)

(52) U.S. Cl.
  CPC ........ *B82Y 35/00* (2013.01); *G01N 33/48721* (2013.01); *G01Q 60/44* (2013.01); *B01L 2300/0896* (2013.01)

(56) References Cited

U.S. PATENT DOCUMENTS

| | | | |
|---|---|---|---|
| 7,708,871 B2 | 5/2010 | Siwy et al. | |
| 7,785,785 B2 | 8/2010 | Pourmand et al. | |
| 8,940,142 B2 * | 1/2015 | Karhanek | G01N 27/4035 204/403.01 |
| 2005/0260119 A1 | 11/2005 | Sunkara et al. | |
| 2008/0237063 A1 | 10/2008 | Chen | |
| 2010/0072080 A1 | 3/2010 | Karhanek et al. | |
| 2011/0136255 A1 | 6/2011 | Dotan et al. | |

OTHER PUBLICATIONS

Siwy et al (Nano Letters, 2006, vol. 6, No. 8, pp. 1729-1734).*
Self-Supporting, Merriam-Webster, https://www.merriam-webster.com/dictionary/self-supporting.*
Yusko (Journal of Physics: Condensed Matter, 22, 2010) (Year: 2010).*
Apel et al ("Diode-like single-ion track membrane prepared by electro-stopping", Nuclear Instruments and Methods in Physics Research Section B: Beam Interactions with Materials and Atoms, vol. 184, issue 3, 2001, pp. 337-346) (Year: 2001).*
Sa ("Reversible Cobalt Ion Binding to Imidazole-Modified Nanopipettes", Analytical Chemistry, 82 (24), 2010, pp. 9963-9966) (Year: 2010).*
Morris et al ("Applications of nanopipettes in the analytical sciences", The Royal Society of Chemistry, 135, 2010, pp. 2190-2202 ) (Year: 2010).*
Choi et al., "Biosensing with conically shaped nanopores and nanotubes", Phys. Chem. Chem. Phys., 2006, 8 4876-4988.
Extended EuropeanSearch Report, Application No. 12754878.2, dated Aug. 26, 2014.
International Search Report and Written Opinion, dated Sep. 28, 2012, PCT/US2012/027531, filed Mar. 2, 2012.
IUPAC Gold Book definition of "polyelectrolyte" downloaded from the web on Nov. 26, 2014.
Karhanek et al., "Single DNA molecule detection using nanopipettes and nanoparticles." Nano Letters, Jan. 2005, vol. 5, No. 2, pp. 403-407.
Laforge, et al., "Electrochemical attosyringe", PNAS, Jul. 17, 2007, vol. 104, No. 29, 11895-11900.
Li, et al., "Development of boronic acid grafted random copolymer sensing fluid for continuous glucose monitoring", NIH Public Access Author Manuscript, from Biomacromoecules, Jan. 2009, 10(1) 113-118, doi:10.1021/bm8009768.
Mulla, et al., "3-Methoxycarbonyl-5-nitrophenyl boronic acid: high affinity diol recognition at neutral pH", Bioorganic & Medicinal Chemistry Letters, 14 (2004) 25-27.
Sa, et al., "Reversible Cobalt Ion Binding to Imidazole-Modified Nanopipettes", Analytical Chemistry, vol. 82, No. 24, Dec. 15, 2010, pp. 9963-9966.
Siwy, "Ion-current rectification in nanopores and nanotubes with broken symmetry", Adv. Fund. Mater., 2006, 16, 735-746.
Shoji, et al., "Potentiometric Saccharide Detection Based on the PKA Changes of Poly(aniline boronic acid)", Journal of the American Chemical Society, vol. 124, No. 42, Jan. 1, 2002, pp. 12486-12493.
Umehara, et al., "Current Rectification with Poly-L-Lysine_Coated Quartz Nanopipettes", Nano Letters, Oct. 2006, vol. 6, No. 11, pp. 2486-2492.
Umehara, et al., "Label-free biosensing with functionalzed nanopipette probes", PNAS, Mar. 24, 2009, vol. 106, No. 12, 4611-4616.
Ying, "Applications of nanopipettes in bionanotechnology", Biochemical Society Transactions (2009) vol. 37, part 4, pp. 702-706.
Zhang, et al., "Covalent Modification of Single Glass Conical Nanopore Channel with 6-carboxymethyl-chitosan for pH Modulated Ion Current Rectification", Electrochemistry Communications, vol. 12,No. 9, Sep. 1, 2010, pp. 1249-1252.

* cited by examiner

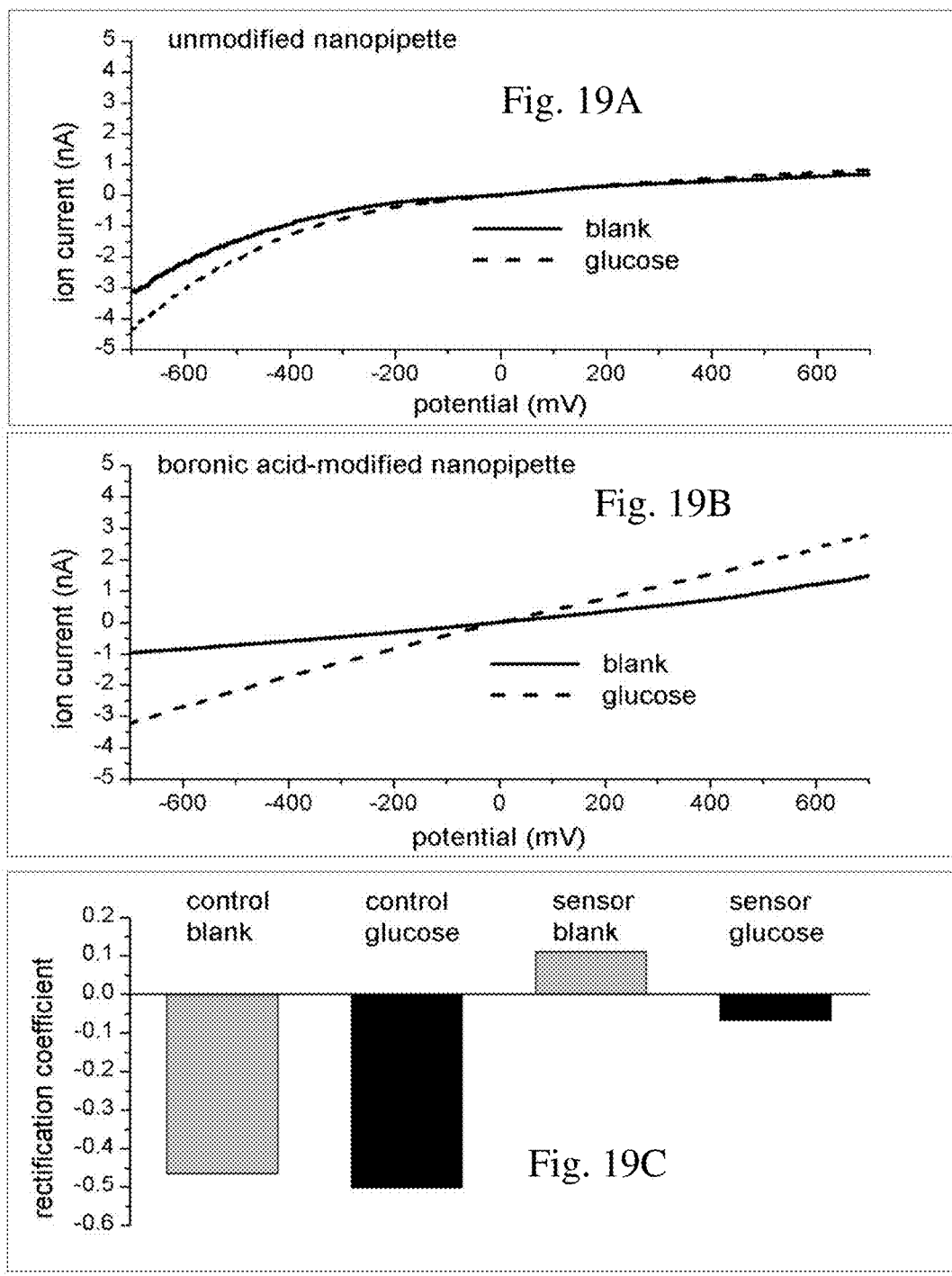

NANOPORE DEVICE FOR REVERSIBLE ION AND MOLECULE SENSING OR MIGRATION

CROSS-REFERENCE TO RELATED APPLICATIONS

This application claims priority from U.S. Provisional Patent Application No. 61/449,379 filed on Mar. 4, 2011, and is a divisional application of U.S. application Ser. No. 13/411,221, filed on Mar. 2, 2012, which are hereby incorporated by reference in its entirety.

STATEMENT OF GOVERNMENTAL SUPPORT

This invention was made with Government support under Contract Number NCC9-165 and NNX08BA47A awarded by the National Aeronautics and Space Administration (NASA), Contract Number P01-HG000205 awarded by the National Institutes of Health, Contract Number NNX09AQ44A awarded by NASA and under Contract Number U54CA143803 awarded by the National Cancer Institute. The Government has certain rights in this invention.

REFERENCE TO SEQUENCE LISTING, COMPUTER PROGRAM, OR COMPACT DISK

None.

BACKGROUND OF THE INVENTION

Field of the Invention

The present invention relates to the field of nanomaterials and specifically to nanopore devices and sensors. In particular, the invention relates to sensing and manipulating and sensing ions and carbohydrates using ionic current measurements on a nanoscale.

Related Art

Presented below is background information on certain aspects of the present invention as they may relate to technical features referred to in the detailed description, but not necessarily described in detail. That is, individual parts or methods used in the present invention may be described in greater detail in the materials discussed below, which materials may provide further guidance to those skilled in the art for making or using certain aspects of the present invention as claimed. The discussion below should not be construed as an admission as to the relevance of the information to any claims herein or the prior art effect of the material described.

Nanopore Ionic Current Modulators

Solid state nanopores are of great interest as stable structures that can be used to mimic biological channels, for the size-selective synthesis of nanoparticles or as nanoscale sensors. Conical, or asymmetric, nanopores are a distinct category of nanochannels that display voltage-gated ion current and can behave as nanofluidic diodes, i.e. they exhibit ionic current rectification. Several groups have developed electrical sensors utilizing ion current measurements across membranes containing asymmetric nanopores (Harrell, C. C. et al., Resistive-pulse DNA detection with a conical nanopore sensor. *Langmuir* 22, 10837-10843, doi: 10.1021/1a061234k (2006); Kececi, K., et al. Resistive-pulse detection of short dsDNAs using a chemically functionalized conical nanopore sensor. Nanomedicine 3, 787-796, doi: 10.2217/17435889.3.6.787 (2008); Sexton, et al., Developing synthetic conical nanopores for biosensing applications. *Mol. Bia Syst.* 3, 667-685, doi:10.1039/b708725j (2007); Au, M., et al. Biosensing with Functionalized Single Asymmetric Polymer Nanochannels, *Macromol. BioscL* 10, 28-32, doi:10.1002/mabL200900198 (2010)). Such devices are generally prepared by a track-etching method. Quartz based nanopores, fabricated from quartz capillaries, exhibit many of the same electrical properties but are rapidly prepared using a laser puller. Quartz conical nanopores, also called nanopipettes, exhibit many properties of other asymmetric nanochannels and are advantageous in that the pore can be manipulated with high spatial resolution, a property that has been used to image cells at the nanoscale.

Investigations with conical nanopores have given rise to new chemical and electrical phenomena that challenge existing ideas about bulk materials. Recently, ion current oscillations were observed with rectifying conical nanopores (2 to 8 nm diameter) in polyethylene terepthalate (PET) films, and were attributed to dynamic precipitation in the pore caused by voltage-induced concentration of weakly soluble salts. Current oscillations in much larger pores of silicon nitride or borosilicate glass can be generated at the interface of two solvents using organic molecules with differential solubility. These phenomena offer a new way to electrically monitor nonequilibrium events such as precipitation in real time and at the nanoscale.

Nanopore Sensors

The stability and ability to mimic biological channels make nanopore-based platforms candidates for studying (bio) molecular interactions. Solid-state nanopores are stable, their diameter can be controlled through the fabrication process and they can be integrated into devices and arrays. Furthermore, their surface properties can be easily tuned by chemical functionalization, allowing the development of chemical and biochemical responsive nanopores. Nanopore-based sensors have incorporated receptors including proteins, DNA, aptamers, ligands, and small biomolecules, allowing a variety of analytes to be targeted. Essential to the sensitivity of many solid-state nanopore sensors is the property of ion current rectification (ICR), arising from the selective interaction between ions in solution and the surface of a charged, asymmetrically shaped nanochannel, or conical nanopore. Nanomaterials exhibiting ICR and used as sensors include track-etched nanopores in polymer membranes and quartz nanopipettes. In either case, a key challenge is the surface modification with appropriate receptors.

Conical quartz nanopores have also been functionalized for sensing applications [See, for example, Sa, N., Fu, V. & Baker, I. A. "Reversible Cobalt Ion Binding to Imidazole-Modified Nanopipettes." *Anal Chem.,* 82, 9663-9666, doi: 10.1021/ac102619j (2010); Fu, Y., Tokuhisa, H. & Baker, I. A. "Nanopore DNA sensors based on dendrimer-modified nanopipettes." *Chem Commun (Comb)*, 4877-4879, doi: 10.1039Jb910511e (2009); Umehara, S., Karhanek, M., Davis, R. W. & Pourmand, N. "Label-free biosensing with functionalized nanopipette probes." *Proceedings of the National Academy of Sciences* 106, 4611-4616, doi:10.1073/pnas.0900306106 (2009); Actis, P., Mak, A. & Pourmand, N. "Functionalized nanopipettes: toward label-free, single cell biosensors." *Bioanalytical Reviews* 1, 177-185, doi:10.1007/s12566-010-0013-y (2010); Actis, P., Jejelowo, 0. & Pourmand, N. "Ultrasensitive mycotoxin detection by STING sensors." *Biosensors and Bioelectronics* 26, 333-337 (2010)].

To date, the reversible binding of analytes with nanopore sensors has proven challenging. However, this is a critical issue if such devices are to be used for applications such as continuous monitoring or repeated measurements with one sensor. Multiple uses for a single sensor will also overcome problems in reproducibly producing pores of the same size, which limits quantitative measurements for many sensors reported in the literature. For such applications, the nanopipette is a promising platform as the sensor tip can be precisely and rapidly manipulated between samples, or within a single sample, with nanoscale precision. To date, functionalized nanopores responsive to pH have shown the best properties in terms of rapidly reversible and selective behavior. Nanopipettes functionalized with imidazole and responding to cobalt ions can be regenerated by immersion in solution of low pH, reprotonating the ligand (Sa, N.; Fu, V.; Baker, L. A., Reversible Cobalt Ion Binding to Imidazole-Modified Nanopipettes. *Anal. Chem.* 2010, 82 (24), 9963-9966).

Transport through nanopores can be modified by a variety of external stimuli including voltage and pressure (see Lan, W.-J.; Holden, D. A.; White, H. S., Pressure-Dependent Ion Current Rectification in Conical-Shaped Glass Nanopores. *J. Am. Chem. Soc.* 2011, 133 (34), 13300-13303.). Simply changing the salt gradient across a nanopore can affect transport, and this effect was used to focus DNA for resistive-pulse measurements (see Wanunu, M.; Morrison, W.; Rabin, Y.; Grosberg, A. Y.; Meller, A., Electrostatic focusing of unlabelled DNA into nanoscale pores using a salt gradient. *Nat Nano* 2010, 5 (2), 160-165.). Nanopores can also be engineered to respond to stimuli such as solvent polarity. This can be achieved with so-called "hairy nanopores," in which the nanopore is decorated with polymers (see Peleg, O.; Tagliazucchi, M.; Kröger, M.; Rabin, Y.; Szleifer, I., Morphology Control of Hairy Nanopores. *ACS Nano* 2011, 5 (6), 4737-4747.). Several artificial nanopores have been engineered for pH-sensitivity using surface modification. Conical nanopores have been modified with receptors for binding other charged species, which likewise modulate current rectification. Targets have included nucleic acids, metal ions, proteins, and small molecules. In the cases of large biomolecules, such as nucleic acids and proteins, physical blocking of the pore likely plays a role in addition to modulation of the surface charge. To date, the modulation of current rectification with small, uncharged species has proved difficult. However, such a system would expand the stimuli for responsive nanopores to include drugs, peptides, and carbohydrates.

Glucose/Diol Sensing

Carbohydrate recognition is essential to monitoring of blood glucose (Kondepati, et al. *Anal. Bioanal. Chem.* 388, 545-563 (2007). Detection and quantification of carbohydrates can also be used in bioprocess monitoring and for medical diagnostics based on metabolic saccharides, nucleotides, or glycoproteins (Timmer, et al. *Curr. Op. Chem. Biol.* 11, 59-65 (2007). Most electrochemical methods for measuring glucose rely on redox enzymes such as glucose oxidase (Oliver, et al. *Diabetic Med.* 26, 197-210 (2009). The most common artificial receptors use boronic acids, which have predominately been used for optical probes (Mader & Wolfbeis, *Microchimica Acta* 162, 1-34 (2008). Non-enzymatic methods for electrochemical measurement of glucose have also been developed, mostly relying on oxidation of glucose (Park, et al. *Anal. Chim. Acta* 556, 46-57 (2006); E. T Chen, Nanopore structured electrochemical biosensors, US 2008/0237063).

To date, there has been very little reported in the literature on nanofluidic pores that respond to carbohydrates. Nanopore analytics have been used to detect small molecules using resistive-pulse methods, but the technique is generally more suited to proteins and other macromolecules. Oligosaccharides on the order of MW 500 to 10,000 have been discriminated using resistive-pulse techniques with alpha-hemolysin pores.

One example of receptor-modified nanopores uses with a covalently attached HRP enzyme, which is then conjugated supramolecularly to Con A, a saccharide-binding protein which interacts with mannose units on the HRP molecule (Ali, et al. *Nanoscale* 3, 1894-1903 (2011). Addition of monosaccharides (galactose and glucose) competes with the Con A, changing the ion current through the pore. Two recent examples make use of boronic acid as a chemical receptor, where the receptor is attached covalently to the walls of artificial nanopores (Sun, Z.; Han, C.; Wen, L.; Tian, D.; Li, H.; Jiang, L., pH gated glucose responsive biomimetic single nanochannels. *Chem. Commun.* (Cambridge, U. K.) 2012.; Nguyen, Q. H.; Ali, M.; Neumann, R.; Ensinger, W., Saccharide/glycoprotein recognition inside synthetic ion channels modified with boronic acid. *Sensors and Actuators B: Chemical* 2012, 162 (1), 216-222.). In the case of the former, an acidic solution was required to reverse the saccharide binding and restore the signal. In the latter, reversible binding was not demonstrated.

Despite many recent advances in nanopore fabrication and surface chemistry, the work cited above shows that there is a need for new schemes to modulate ion current using carbohydrates as an external stimulus. This problem may be addressed with new functional materials that can interface with nanopores.

Specific Patents and Publications

Karhanek et al. in US Patent Application Publication 2010/0072080, published on Mar. 25, 2010, disclose methods and devices comprising a nanopipette having thereon peptide ligands for biomolecular detection, including of peptides and proteins.

Siwy et al. in U.S. Pat. No. 7,708,871, issued on May 4, 2010, disclose an apparatus having a nanodevice for controlling the flow of charged particles in an electrolyte. Such apparatus comprises an electrolytic bath container divided by a polymeric membrane foil for controlling the flow of charged particles in an electrolyte.

Sa et al. in Analytical Chemistry 2010, 82 (24), pp 9963-9966 disclose that quartz nanopipettes modified with an imidazole-terminated silane respond to metal ions ($Co^{2+}$) in solution. The response of nanopipettes was evaluated through examination of the ion current rectification ratio. When nanopipettes were cycled between solutions of different pH, adsorbed $Co^{2+}$ was released from the nanopipette surface, to regenerate binding sites of the nanopipette.

Umehara et al. in Proceedings of the National Academy of Sciences, vol 106, pages 4611-4616, Mar. 24, 2009, disclose a label-free, real-time protein assay using functionalized nanopipette electrodes. Electrostatic, biotin-streptavidin, and antibody-antigen interactions on the nanopipette tip surface were shown to affect ionic current flowing through a 50-nm pore.

Umehara et al. "Current Rectification with Poly-L-lysine Coated Quartz nanopipettes," Nano Lett. 6(11):2486-2492 (2006) discloses current responses of noncoated and Poly-l-lysine coated nanopipettes using a nanopipette in a bath solution.

Karhanek M., Kemp J. T., Pourmand N., Davis R. W. and Webb C. D, "Single DNA molecule detection using nanopipettes and nanoparticles," Nano Lett. 2005 February; 5(2):403-7 discloses that single DNA molecules labeled with nanoparticles can be detected by blockades of ionic current as they are translocated through a nanopipette tip formed by a pulled glass capillary. The disclosed set up uses a voltage clamp circuit, which utilized a single detecting electrode in a bath to detect nanoparticle-DNA current block.

Ying, Liming in Biochemical Society Transactions, vol 37, pages 702-706, 2009, reviews nanopipettes and their use in nanosensing and nanomanipulation of ions, molecules (including biomolecules) and cells.

Borghs, Gustaaf, et al. in WO 2006/000064, published on Jan. 5, 2006, disclose a nanofluidic device for controlling the flow of charged carriers through a nanopore extending through a membrane.

Sunkara, et al. in US Patent Application Publication 2005/0260119, published on Nov. 24, 2005, disclose a method of synthesizing tubular carbon nanostructures in the form of tapered whiskers, termed nanopipettes, using microwave plasma assisted chemical vapor deposition method.

Chen US 20080237063 published Oct. 2, 2008, entitled "Nanopore structured electrochemical biosensors," discloses a biosensor having a nanopore structured and catalytically active cyclodextrin attached thereto for direct measurement of glucose.

Choi et al., "Biosensing with conically shaped nanopores and nanotubes," Phys. Chem. Chem. Phys. 8:4976-4988 (2006) discusses the preparation and characterization of conical nanopores synthesized using a track-etch process. The design and function of conical nanopores that can rectify the ionic current that flows through these pores under an applied transmembrane potential is also disclosed.

Li et al., "Development of boronic acid grafted random copolymer sensing fluid for continuous glucose monitoring," Biomacromolecules 10(1):113-118 (2009) discloses biocompatible copolymers poly(acrylamide-ran-3-acrylamidophenylboronic acid) (PAA-ran-PAAPBA) for viscosity based glucose sensing.

Sun, Z.; Han, C.; Wen, L.; Tian, D.; Li, H.; Jiang, L., pH gated glucose responsive biomimetic single nanochannels. *Chem. Commun.* (Cambridge, U. K.) (2012) describe a track-etched conical nanochannel in polyethylene teraphthalate (PET) covalently modified with phenylboronic acid receptors.

Nguyen, Q. H.; Ali, M.; Neumann, R.; Ensinger, W., Saccharide/glycoprotein recognition inside synthetic ion channels modified with boronic acid. *Sensors and Actuators B: Chemical* 2012, 162 (1), 216-222.) describe a track-etched conical nanochannel in polyethylene teraphthalate (PET) covalently modified with phenylboronic acid receptors. The channel responds to monosaccharides as well as glycoproteins.

BRIEF SUMMARY OF THE INVENTION

The following brief summary is not intended to include all features and aspects of the present invention, nor does it imply that the invention must include all features and aspects discussed in this summary.

The present invention, in certain aspects, is directed to a nanopipette for use in an apparatus detecting an analyte in a sample, comprising a capillary portion defining an interior bore of the nanopipette leading to a nanopore opening; said interior bore adapted for containing therein an electrode and adapted to contain an interior solution communicating with an exterior solution through said nanopore (see, for electrode configuration, e.g. FIG. 1, where the bore is elongated and tapers to the opening); and a coating on an interior surface of the nanopore, comprising a polyelectrolyte bound directly to (i.e. contacting) said interior surface (typically quartz); and a binding molecule, linked to said polyelectrolyte, specific for binding an analyte selected from the group consisting of an ion or a small molecule.

In certain aspects of the present invention, the binding molecule linked to the polyelectrolyte may be a boronic acid for sensing glucose, and/or the polyelectrolyte may be a polycation whereby the charge of the coating changes; and/or the polyectrolyte may be polyalkyl pyridine or a polyamine.

In certain aspects, the present invention, the polyelectrolyte/sensing molecule is applied to the nanopore so as to extend into and partially block the nanopore, exposing more of the sensing molecule to the sample.

In certain aspects of the present invention, the binding molecule is a chelating agent linked to a polymer or polyelectrolyte coating. The polymer coating may further comprise a polyelectrolyte layer between the pipette bore and the ion binding polymer. The layer may be in the form of a coating, and preferably is continuous, whereby bare quarts is covered. In some embodiments, the chelating agent may be an ion binding polymer which is a polysaccharide, for example, chitosan, a linear polysaccharide. In some embodiments, the chelating agent may be a polypeptide. In some other embodiments, the coating may comprise a saccharide binding molecule. In some embodiments, the saccharide binding molecule may be a protein, such as a lectin. In some embodiments, the saccharide binding molecule comprises boronic acids or boronic esters.

In a further embodiment, the present invention comprises a nanopipette device for sensing carbohydrate molecules, in particular carbohydrates with cis-diol groups, and, more particularly, glucose. The device may comprise an inert substrate bearing a nanopore in which the nanopore comprises a channel. In certain aspects, the channel is a quartz nanochannel. In some aspects, the inert substrate defines an interior portion accessed through the channel and an exterior portion for contacting with a sample. In some aspects, the nanopore further comprises a polymeric coating within the channel, said polymer linked to a carbohydrate-binding molecule ("CBM," such as boronic acid). In some aspects, the nanopore further comprises a polymer linked to said CBM, wherein the CBM is embedded within the polymer to form a semi-permeable matrix within the channel.

The device is operated with a measuring circuit in which ionic current rectification by ionic conditions at the nanopore is modulated by binding of the glucose analyte. In a preferred embodiment, binding of a saccharide to the polymer-linked boronic acid causes a reversal of ionic rectification. Thus, the device may comprise an electronic circuit for producing a current through the channel and measuring changes in current flow through the channel, whereby carbohydrate molecules in said sample bind to said CBM, resulting in a measured change in current flow indicative of carbohydrate presence in the sample.

In some aspects, the present invention comprises a nanopipette measuring circuit comprising a nanopipette having an interior electrode, a bore for holding an interior solution, a container for an exterior solution, and a measuring circuit between the interior electrode and an external electrode adapted and located to be in contact with an exterior solution, wherein the measuring circuit comprises an amplifier for delivering a reversible voltage differential between said interior electrode relative to the external electrode, and further comprises a detector for measuring current between the bore and the exterior solution.

Certain aspects of the invention are concerned with methods for creating ionic compounds by combining two different ions in solution, i.e. a nanoscale reactor, comprising steps of providing at least one first ion having a charge in a solution inside of a nanopipette with a nanopore between an interior of the nanopipette and an exterior solution; providing a second ion species in the exterior solution; and applying to the one ion having a charge in a solution inside of a nanopipette a voltage across the nanopore of opposite charge, said voltage sufficient to cause migration of said ion species to the nanopore to react with said second ion to form said ionic compound. In some embodiments, the change in current indicative of formation of the ionic compounds may be oscillations.

In certain aspects, the present methods further comprise the step of measuring ionic current through the nanopore and detecting a change in current indicative of formation of the ionic compound.

In some embodiments, the ionic compounds are insoluble. The method may further comprise the step of reversing the voltage after a precipitate has formed.

The first or second ions may be a metal ion reacting with an anion to form the ionic compound. The metal may be a transition metal. The metal ion from the group consisting of $Mg^{2+}$, $Ca^{2+}$, $Mn^{2+}$, $Zn^{2+}$, $Cu^{2+}$, $Fe^{2+}$, $Fe^{3+}$, $Cr^{3+}$, $Cr^{6+}$, $Cd^{2+}$, $Mo^{2+}$, $Co^{3+}$, $Co^{2+}$, $Hg^{2+}$, $Ni^{2+}$, $Al^{3+}$, $Al^{2+}$, $Ar^{3+}$, $Ar^{3-}$ and $Pb^{2+}$. The anion may be from the group consisting of phosphate, chloride, sulfate, monophosphate, pyrophosphate, metaphosphate, tripolyphosphate, tetrametaphosphate, and orthophosphate. In some embodiments, the anion may be selected from the group consisting of organic carboxylic acid anions selected from the group consisting of gluconate, tartrate, fumarate, maleate, malonate, malate, lactate, citrate, EDTA, citraconate, citramalate, stearate, oleate, laurate, octoate ascorbate, picolinate, and orotate. In some other embodiments, the anion may be a protein.

In certain aspects, the present invention is directed to a method of delivering an ion into an exterior solution from inside a nanopipette comprising providing at least one first ion having a charge in a solution inside of a nanopipette with a nanopore between an interior of the nanopipette and an exterior solution; and applying a voltage across the nanopore of opposite charge to said first ion, said voltage sufficient to cause migration of the ion across the nanopore.

BRIEF DESCRIPTION OF THE DRAWINGS

FIG. 18A shows covalent attachment of receptors directly to the nanopore wall. FIG. 18B shows adsorption of a functional polymer to the pore wall, with receptors linked to the polymer. FIG. 18C shows Immobilization of a three-dimensional functional matrix inside the pore, where receptors on the polymer form a mesh-like network across the nanopore, ie. the coating extends into and partially blocks said nanopore.

FIGS. 19A, 19B and 19C is a set of graphs showing the response of control and functionalized pipette with glucose (3 mM) in pH 7 phosphate buffer. The pipette was functionalized with 3-aminopropyl triethyxysilane followed by m-bromomethylphenylboronic acid. Inset: rectification coefficients calculated from the ion current at +500 and −500 mV. FIG. 19A is a graph showing ion current response of an unmodified pipette; FIG. 19B is a graph showing ion current response of a boronic acid-modified pipette and FIG. 19C is a graph showing rectification of the pipette systems shown in FIGS. 19A and B.

FIGS. 26 and 27 were enerated by titrations of fructose into a probe solution containing PVP-BA (0.003% w/v) and HPTS (1.5 µM) in pH 9.5 carbonate buffer with 25% methanol. Error bars show the standard deviation from three separate titrations. Graph B shows the ion current at potential −500 mV for conical nanochannel embedded with PVP-BA with increasing concentrations of fructose in a carbonate buffer. Error bars show standard deviation from 5 sequential voltage scans. Data points were fitted to binding isotherm as described in the experimental section.

DETAILED DESCRIPTION OF THE PREFERRED EMBODIMENT

Overview

Figure 1:
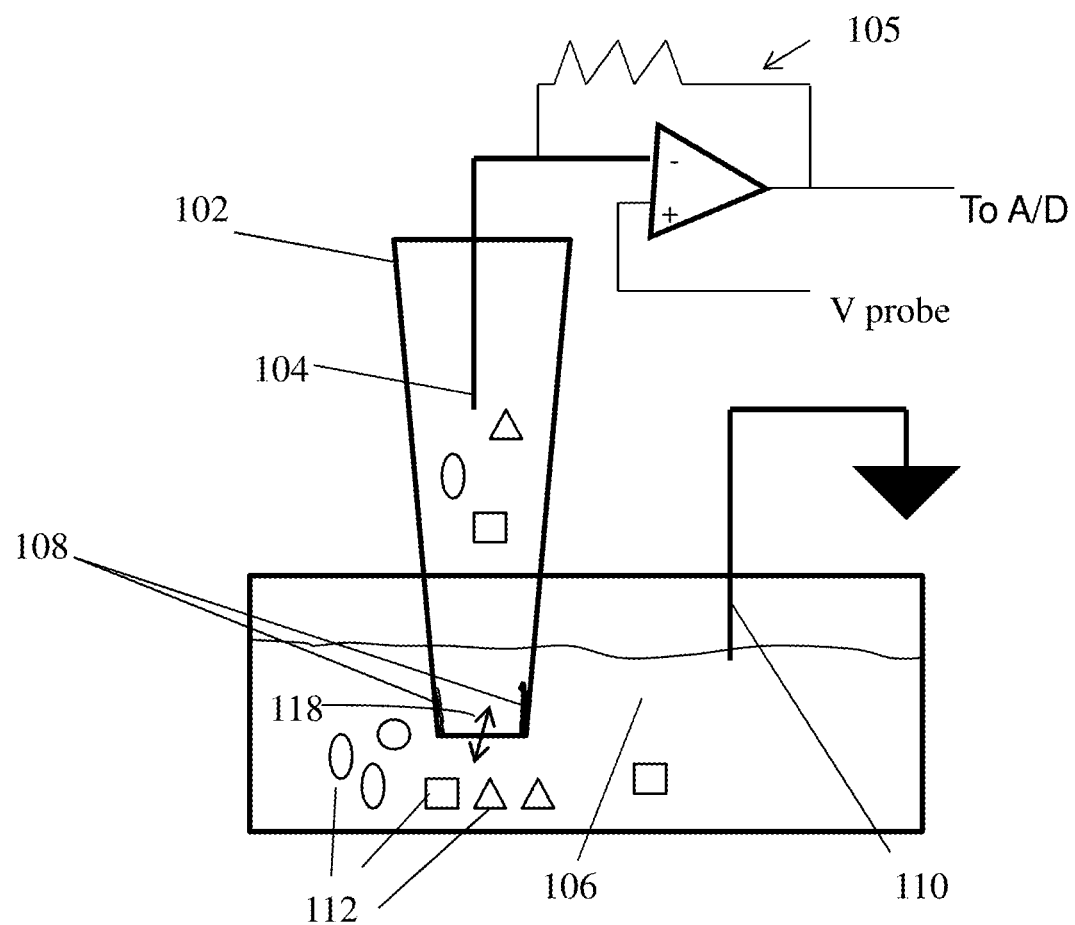
FIG. 1 is a schematic representation of the electrochemical setup and the reversible binding of cupric ions on a sensor that has been functionalized to specifically bind such ions in the vicinity of the interior of the nanopipette, near the tip.

The present invention relates to a nanopore device, i.e. a nanopipette, which is comprised in an electrochemical sensor. The device is configured to contain an interior region that contains a first electrode, and to be contacted with an external solution that contains another electrode. These electrodes are connected to a sensing circuit where phenomena occurring at the nanopore may be detected and measured. In the preferred embodiment, the nanopore is part of a nanopipette, as described for example in the above referenced US 2010/0072080 from the same assignee. The term "nano" refers to dimensions within the bore, and the accompanying parts, such as the interior electrode, which will have a diameter on the order of <200 nm. The present dimensions are important for creating the electrochemical behavior described in detail below.

The present invention further relates to a reversible ion sensor that can bind and detect the binding of small ions such as H+ and metal cations, as well as diols (discussed below). The reversible sensor is reversible in terms of reversing polarity within the sensor cavity (i.e. nanopipette bore) and, importantly, in that the ions are bound to the nanopore in a reversible manner. The present device can be used to cause migration of ions within the sensor and out of the sensor nanopore, which sensor preferably is in the form of a nanopipette. The binding of ions within the pipette can be reversed by immersion of the pipette tip in a solution free of the bound ion. Binding of the small ions can also be released by changing conditions such as pH in the solution. The present invention also relates to a reversible ion migration device based on a nanopipette. Such ion migration can be induced by changes in voltage potential inside the nanopipette relative to the external solution. Ion migration can be used to induce precipitation caused by migration of ions out of the nanopipette bore to create excess ions in the external solution. The precipitation occurs in the vicinity of the nanopore tip of the nanopipette and can be detected at an early stage by changes in current oscillations through the nanopore at the tip. The precipitation causes changes in an ion current through the nanopore tip induced by an applied voltage potential between the interior and the external solution. The precipitation that is detected at small ion concentrations and at small precipitate sizes can be applied to a variety of systems. For example, protein crystallization can be detected using small amounts of protein.

The present sensor technology relies on a simple electrochemical readout that can transduce, in a label-free manner, binding events at the tip of the functionalized nanopipette. The high impedance of the nanopipette tip confines the sensitivity of the device, making the dimension and geometry of the tip orifice crucial for the sensor performance. Furthermore, the present sensor technology can be easily integrated with piezoactuators to generate a sensor with high spatial resolution. As a nanopipette approaches a surface, the ionic current through the pipette will decrease due to "current squeezing", a well known effect, exploited to great benefit in scanning ion conductance microscopy (SICM). Besides sensing, nanopipette based platforms have been used to investigate single-molecule biophysics, for the controlled delivery of molecules inside a single cell, and to image cells at the nanoscale.

In certain embodiments, the present devices present a new mechanism for inducing and/or measuring current oscillations using precipitation in a solid-state nanopore. The technique can be used to actively direct ion migration to the interface of two solutions at the tip of a nanopipette. Because the pore becomes blocked only at a threshold potential, the reaction can be controlled temporally as well as spatially. Such precipitation can be carried out with a variety of ions. This ability to control and measure the kinetics of salt precipitation at the nanoscale enables new techniques for studying dynamic processes such as biomineralization and dissolution. The trapping of a precipitate within the nanoreactor by voltage oscillations is a further tool to study size and surface charge of nanoparticles. The controlled nanoprecipitation of insoluble salts is also valuable in developing selective and sensitive ion sensors. The reactions described below were able to detect as little as 2 micromolar salt, and were unaffected by the presence of other cations. For example, a low concentration (up to 2 µM) of zinc sulphate salt was detected and was unaffected by the presence of other cations such as potassium or magnesium. Furthermore, the ability for a nanopore blocked by precipitation to be opened through oscillating potentials can expand the applications for sensing with nanopores. For example, a constant voltage may be used to detect nanoprecipitates, while oscillating potentials can be used to measure ion current for other sensing applications.

The present methods may be used in a variety of protein crystallization methods. Different crystallization methods are used to bring a protein solution into supersaturation, normally through a gradual decrease of solubility of the protein. The most common way to reduce protein solubility in protein crystallization is by the addition of precipitants such as polyethylene glycol and ammonium sulfate. The precipitant binds water as its concentration is increased, for example by using the method of vapor diffusion. As a result, the amount of solvent available for the protein is decreased, which essentially means that the concentration of the protein is increased. At a certain effective protein concentration, it will begin to precipitate, creating a crystal if conditions are correct. The correct crystallization conditions, which include a combination of a right pH, ionic strength, temperature, protein concentration, the presence of various salts, ligands or additives, the type of precipitant and the actual crystallization method (hanging drop, sitting drop, dialysis, etc.), are practically impossible to predict in advance; as a result, crystallization screens using different conditions have been developed. The present device may be employed in a number of parallel experiments to test the effect of different protein crystallization conditions.

Another application of the present method is in the field of analytical ion sensing. For what is believed to be the first time, the analytical application of chemically functionalized solid-state nanopores is shown for ion sensing. The frequency and the waveform of the applied voltage were found to be adjustable to maximize the signal-to-noise ratio, showing that the applied voltage could trigger the $Cu^{2+}$ binding on the sensor. The ability to temporally and spatially direct the binding of molecules allows for the development of precise biosensing devices capable of studying thermodynamic and kinetic properties of the analyte-receptor interaction.

The biosensors disclosed herein show selective and reversible binding in a rectifying nanopore. This type of reversible sensor overcomes the challenges associated with making nanopores of unified pore structures in ICR-based sensors. Monitoring the deposition of polyelectrolyte layers effectively ensures that farther chemical modifications are localized to the pore where ICR is the most sensitive. Further experiments and theoretical modeling, as well as advanced methods of characterizing nanopore surfaces will be required to determine how far into the pore the polyelectrolytes penetrate and further explore interactions at the interface of bulk solutions and the outer nanopipette pore. Progress in this area will advance the use of nanopore sensors as analytical tools. Reversible nanopipette sensors such as those described here may be used for monitoring of water quality, spatial resolution of ion concentration at the nanoscale (functional mapping) or continuous intracellular measurements of specific analytes.

The present devices have been adapted for glucose sensing as may be needed by subjects at risk for diabetes. They can be built as portable devices that can be applied to whole blood from or even in a subject in need of glucose monitoring. That is, for example, quartz nanopipette tips can penetrate the skin to contact glucose in body fluid in the vicinity of the dermis.

The present glucose-sensing devices preferably employ a polymer which is bound to a receptor such as boronic acid (a receptor for saccharides) and the mixture applied to the interior surface of the nanopipette, at or near the tip (nanopore). The saccharide-binding polymer mixture most preferably has the following properties: 1) The polymer is positively charged so as to increase interaction with the negatively charged pore walls. 2) The polymer will have approximately one boronic acid for each positive charge, resulting in a neutralization of the polymer on conversion to boronate form. 3) The polymer is soluble in organic solvents but insoluble in aqueous media, such that the polymer can be trapped in the tip of the nanopipette. 4) The insoluble matrix formed by the polymer is permeable to water, ions, and analytes. 5) No change in solvent or media should be required to reverse signal modulation in the sensor.

The permeable matrix method is thought to be superior to other nanopore functionalization methods because the entire volume of the nanopore, rather than only the pore walls, contains the receptor. The polymer-bound receptors (e.g. boronic acid) will have greater interaction with ions travelling through the nanopore, and thus give higher signal modulation in the presence of the analyte. Furthermore, many polymers undergo changes in conformation upon analyte binding, which may further enhance ion current modulation. Finally, it is important to note that the analyte does not need to be driven through the pore by an electric field—rather, passive diffusion of the analyte through the polymer matrix will modulate the electrical signal. These features distinguish an immobilized polymer network from covalent attachment of a receptor or layer-by-layer deposition of functionalized polymers. A system based on poly-(4-vinylpyridine) (PVP) was chosen, as described below.

Figure 26:
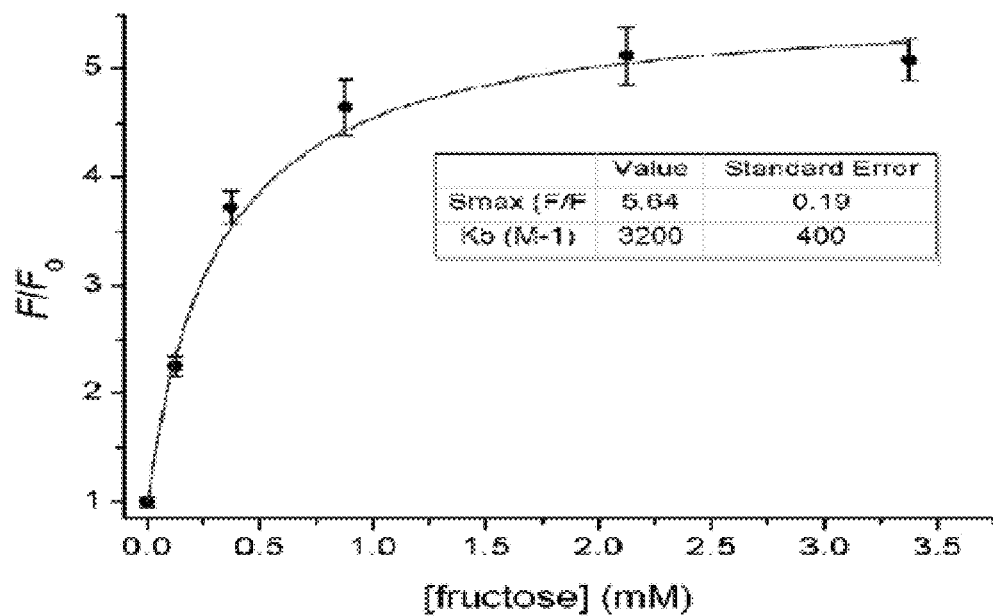
FIG. 26 is line graph showing binding isotherms for fructose using PVP-BA in a solution-phase fluorescence assay.

As described in detail below, a nanopipette device was fabricated in which functional polycation containing boronic acid glucose receptors were embedded in a quartz nanochannel. Previous efforts to directly modify the walls of nanochannels (i.e. nanopores) with boronic acids have resulted in modest response to saccharides, but there are several aspects of boronic acid-based receptors that should offer much greater control over ionic current. First, the binding of boronic acids to carbohydrates is completely reversible, and there is no evidence that this is the case in a nanochannel. More importantly, boronic acids can undergo a change in electrostatic charge in the presence of neutral carbohydrates—a change which should dramatically affect current rectification in a nanopore. To take advantage of these properties for an engineered nanochannel, a cationic polymer based on poly(4-vinylpyridine) was chosen as a boronic acid receptor matrix (FIG. 26). Alkylation of the polymer produces exactly one boronic acid for every positive charge. The cationic polymer can be immobilized to the quartz nanopipette based on electrostatic interaction, an interaction that can be monitored based on current rectification.

Boronic acids as used here are simple artificial receptors that have been recognized for their ability to bind saccharides. There are several properties of the boronic acid that can be exploited to make sensors and actuators. On binding 1,2-diols (e.g. 1,2 dihydroxy benzene, ethylene glycol), the Lewis acidity of the boronic acid is increased. For example, phenyl boronic acid forms a complex with catechol (1,2 benzenediol) in equilibrium with negatively charged boron species (See, Artificial Receptors for Chemical Sensors, edited by Vladimir M. Mirsky, Anatoly Yatsimirsky, Wiley-CH, Chapter 6 (2011)). Thus, if the $pK_a$ is shifted to a value lower than the pH of the buffering medium, binding of a carbohydrate results in conversion of the boronic acid to the anionic boronate ester. Many of the probes and sensors reported to date using boronic acids are fluorescence-based. Because of the versatility of boronic acids, however, this receptor has also been used for carbohydrate separations, optical sensors based on swelling of polymeric materials, and electrochemical sensors. The fact that binding a neutral saccharide can effect a change in the charge of boronic acids makes this receptor an excellent candidate for engineering responsive nanofluidic diodes.

Modified nanopores within nanochannels showed strong current rectification resulting from the cationic charge of the polymer, a rectification that can be inverted in the presence of neutral carbohydrates. The nanochannels showed reversible behavior with millimolar concentrations of fructose. The ability to characterize the polymer in solution showed a binding mode dependent both on the interaction of 1,2-diols with boronic acids, as well as electrostatic charge. Modified nanochannels showed especially high sensitivity to the anionic catechol-containing dye, alizarin-red sulfonate (ARS), with cancellation of current rectification using only 60 μM dye. Importantly, the modulation of ion permeability relied not on blocking ion conductance, but in changing the polarity of current rectification as a result of electrostatic charge. This application will enable new techniques independent of voltage for modulating ion flow through nanochannels.

Definitions

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification. For purposes of the clarity, following terms are defined below.

The term "ion" means an atom or molecule in which the total number of electrons is not equal to the total number of protons, giving it a net positive or negative charge, The term refers specifically to an atomic or a monoatomic ion, where the ion consists of a single atom, and to polyatomic ions of small molecules.

The term "small molecule" means a compound having a molecular weight of less than about 1,000 atomic mass units, or, in some embodiments less than 200 amu. Small molecules do not include polynucleic acids or polypeptides above the size limit, but include other small molecules typically found in a cell. By way of example, adenine is about 135 amu; glucose is about 180 amu; urea is about 60 amu; creatinine is about 113 amu.

The term "nanopipette" means a hollow self-supporting, inert, non-biological structure with a conical tip opening of nanoscale, i.e., a nanopore, having a tip opening of 0.05 nm to about 500 nm, preferably about (+ or −20%) 50 nm or about 80 nm or about 100 nm. The hollow structure may be e.g. glass or quartz, and is suitable for holding inside of it a fluid which is passed through the tip opening. The interior of the nanopipette is selected or modified to minimize nonspecific binding of analyte. The interior of a nanopipette typically is in the form of an elongated cone, with a uniform wall thickness of a single layer of quartz or other biologically inert material, and is sized to allow insertion of an electrode that contacts solution in the nanopipette. The nanopipettes used herein typically have a single bore, but nanopipettes with multiple concentric bores can be prepared by pulling dual bore capillary tubes. The outer diameter is typically less than about 1 μm in the tip region.

The term "nanopore" means a small hole in an electrically insulating membrane, preferably the tip of a nanopipette, as described. The nanopore will be in a tip region, which is the last few mm of the nanopipette bore, adjacent the nanopore. The nanopore, as described below, is sized so that small molecular complexes will affect movement of ions and molecules through the nanopore. The nanopore is designed to function in a device that monitors an ionic current passing through the nanopore as a voltage is applied across the membrane. The nanopore will have a channel region formed by the nanopipette body, and, preferably, will be of a tapered, e.g. frusto-conical configuration. By pulling a quartz capillary as described below, a reproducible and defined nanopore shape may be obtained.

The term "current rectification" means an effect when charged nanopores respond to a symmetric input voltage with an asymmetric current output. When the diffuse electrical double layer thickness is comparable with the pore size, the electrostatic interactions between fixed charged species on the nanopore surface and ionic species in solutions alters nanopipette permselectivity. The rectification coefficient, r, is defined as the logarithm of the ratio between the current measured at particular positive voltage and the current measured at the same voltage but with the opposed polarity, i.e. $r=\log_{10} I+/I-$.

This coefficient is a useful indicator of the rectifying properties of a nanopipette and therefore of the fixed charges on the sensor surface. Quartz nanopores, being negatively charged, show a negative current rectification ($r<0$). The rectification can be inverted ($r>0$) by modifying the nanopore surface with charged functional layers such as poly-L-lysine, dendrimers, aminosilane and chitosan.

The term "nanopipette apparatus" means a nanopipette operatively connected to a current detecting circuit and adapted to receive a sample fluid in contact with the nanopipette and any reference electrode.

The term "current detecting circuit" means a device for detecting current and/or voltage, and applying same in a circuit, such as connected to a nanopipette and a reference electrode as described herein. The circuit may comprise any sensitive device for detecting changes in current on the order of 1-100, 10-100 or 1-10 picoamperes, based on a baseline current of 10-10000 picoamperes. The term further refers to a circuit that is time responsive and relatively temperature independent or allow for changes in temperature to be compensated for. It should have an input in a circuit where a known voltage is supplied. Sensitive detecting circuits are known, including voltage clamp amplifiers and transimpedance amplifiers. The term "voltage clamp" here refers to circuits which utilize a differential amplifier having one input connected to a variable command voltage, another input connected to a measured voltage, and a feedback circuit. The voltage clamp uses negative feedback to maintain the system at the command voltage, which in this case is a predetermined alternating signal, such as an alternating voltage signal from a signal generator. The output current follows changes in the input voltage and small changes in current can be detected.

The term "quartz" means a nanopipette media is a fused silica or amorphous quartz, which is less expensive than crystalline quartz. Crystalline quartz may, however, be utilized. Ceramics and glass ceramics and borosilicate glasses may also be utilized but accuracy is not as good as quartz. The term "quartz" is intended and defined to encompass that special material as well as applicable ceramics, glass ceramics or borosilicate glasses. It should be noted that various types of glass or quartz may be used in the present nanopipette fabrication. A primary consideration is the ability of the material to be drawn to a narrow diameter opening. The preferred nanopipette material consists essentially of silicon dioxide, as included in the form of various types of glass and quartz. Fused quartz and fused silica are types of glass containing primarily silica in amorphous (non-crystalline) form.

The term "electrolyte" means a material that contains electrolyte solids, i.e., free ions. Typical ions include sodium, potassium, calcium, magnesium, chloride, phosphate and bicarbonate. Other ionic species may be used. The material will typically be liquid, in that it will comprise the sample, containing the analyte, and the ions in solution. The sample itself may be an electrolyte, such as human plasma or other body fluids, water samples and so on. The electrolyte should carry an ionic current; about 10-100 mM, preferably about 100 mM of positive and negative ionic species are thought to be required for this function. The present device may employ either the same or different electrolytes in the nanopipette interior and in the sample material.

The term "polyelectrolyte" is used herein in its conventional sense, i.e. polymers whose repeating units bear an electrolyte group. These groups will dissociate in aqueous solutions (water), making the polymers charged. Polyelectrolyte properties are thus similar to both electrolytes (salts) and polymers (high molecular weight compounds), and are sometimes called polysalts. Like salts, their solutions are electrically conductive. Like polymers, their solutions are often viscous. Charged molecular chains, commonly present in soft matter systems, play a fundamental role in determining structure, stability and the interactions of various molecular assemblies. Polyelectrolytes include biological polymers which contain charged functional groups and synthetic polymers. Examples of polyelectrolytes of biological origin include, but are not limited to, oligonucleotides, nucleic acids, proteins, peptides, polysaccharides like pectin, carrageenan, alginates, and chitosan. Examples of synthetic polymers include, but are not limited to, polyvinylpyrrolidone, carboxymethylcellulose, poly (sodium styrene sulfonated), polyacrylic acid, etc.

The charges on a polyelectrolyte may be derived directly from the monomer units or they may be introduced by chemical reactions on a precursor polymer. For example, poly(diallyidimethylammonium chloride) ("PDAD") is made by polymerizing diallyidimethylammonium chloride, a positively charged water soluble vinyl monomer. The positively-charged copolymer PDAD-co-PAC (i.e., poly(diallyidimethylammonium chloride) and polyacrylamide copolymer) is made by the polymerization of diallyidimethylammonium chloride and acrylamide (a neutral monomer that remains neutral in the polymer). Poly(styrenesulfonic acid) can be made by the sulfonation of neutral polystyrene. Poly(styrenesulfonic acid) can also be made by polymerizing the negatively charged styrene sulfonate monomer.

Various polyelectrolytes comprising polyanions may be used in the present invention. Weak polyanions typically include carboxylic acid groups while strong polyanions typically include sulfonic acid groups, phosphonic acid groups, or sulfate groups. Examples of a negatively-charged polyelectrolyte include polyelectrolytes comprising a sulfonate group ($—SO_3$), such as poly(styrenesulfonic acid) ("PSS"), poly(2-acrylamido-2-methyl-1-propane sulfonic acid) ("PAMPS"), sulfonated poly(ether ether ketone) ("SPEEK"), sulfonated lignin, poly(ethylenesulfonic acid), poly(methacryloxyethylsulfonic acid), their salts, and copolymers thereof; polycarboxylates such as poly(acrylic acid) ("PAA") and poly(methacrylic acid); and sulfates such as carrageenin. Other polyanions include HV-sodium alginate, sodium alginate, sodium hyaluronate, heparin sulfate, cellulose sulfate, kappa carrageenan, pentasodium tripolyphosphate, low-esterified pectin (polygalacturonic acid), polyglutamic acid, carboxymethylcellulose, chondroitin sulfate-6, chondroitin sulfate-4, and collagen. The molecular weight and charge density of the polyanions are selected such that the compounds form polyelectrolyte complexes with a suitable polycation.

Various polyelectrolytes, which are polycations, may also be employed as cationic polymers. Exemplary polycations include polyalkylene imines, such as polyethylene imine ("PEI") and polypropylene imine. Other polycations include polyamines, i.e. polymers in which the monomer units have pendant amine groups, such as polyethylene polyamine, polypropylene polyamine, polyvinylamine, polyallylamine, poly(vinylalcohol/vinylamine), chitosan, polylysine, polymyxin, spermine hydrochloride, protamine sulfate, poly(methylene-co-guanidine) hydrochloride, polyethylenimine-ethoxylated, polyethylenimine-epichlorhydrin modified, quarternized polyamide, and polydiallyidimethyl ammonium chloride-co-acrylamide. As is known in the art, chitosan is a linear polysaccharide composed of randomly distributed β-(1-4)-linked D-glucosamine (deacetylated unit) and N-acetyl-D-glucosamine (acetylated unit)

Figure 16:
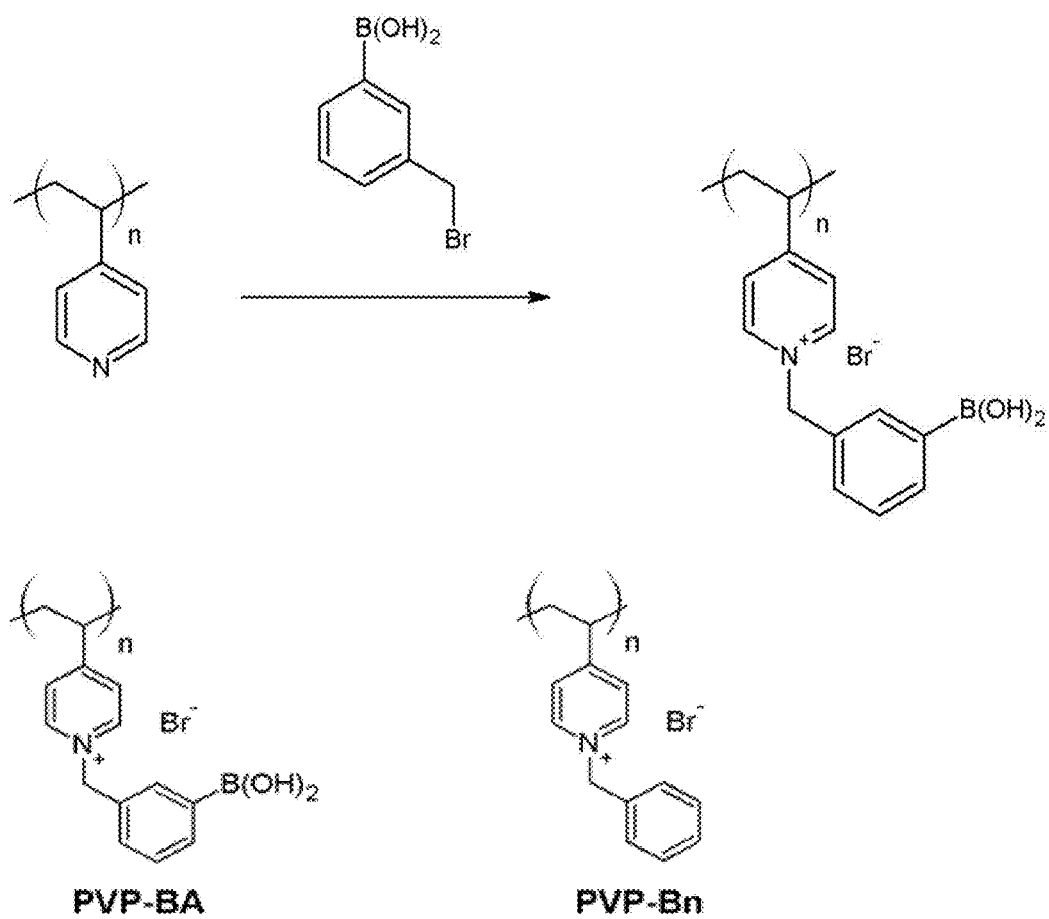
FIG. 16 is a diagram showing the synthesis of a cationic polyelectrolyte for modification of a nanopipette. The polycation is represented by repeating pyridyl units on an alkyl backbone.

Other examples of a positively-charged polyelectrolytes include quaternary ammonium group, such as poly(diallyidimethylammonium chloride) ("PDAD"), poly(vinylbenzyltrimethyl-ammonium) ("PVBTA"), ionenes, poly(acryloxyethyltrimethyl ammonium chloride), poly(methacryloxy(2-hydroxy)propyltrimethyl ammonium chloride), and copolymers thereof; polyelectrolytes comprising a pyridinium group, such as, poly(N-methylvinylpyridine) ("PMVP"), other poly(N-alkylvinylpyridines), and copolymers thereof; and protonated polyamines such as poly(allylaminehydrochloride) ("PAH"). The molecular weight and charge density of the polycations are selected such that the compounds form polyelectrolyte complexes with a suitable polyanions. Further description of an pyridyl-based cationic polymer may be found e.g. in U.S. Pat. No. 4,384,075, "Cationic Alkenyl Azabenzenes and Rubber Modified Asphalts." Polyvinylpyrimidines such as Poly(4-vinylpyridine) (Mw ~60,000), exemplified below, and, e.g. Poly(4-vinylpyridine-co-butyl methacrylate) are also explicitly defined as cationic polymers. Any of several groups can be used to alkylate the pyridyl-based polymer and produce a polycation. The groups can contain receptors such as boronic acid, biotin, and chelating ligands. Therefore, as is understood in the art, the present polyelectrolyte may be a polyalkyl pyridine. i.e. a polymer having an alkyl backbone with pendant pyridyl groups. A polyalkyl pyridine will typically have, as shown in FIG. 16, an alkyl (e.g. vinyl) backbone of "n" repeating units, depending on molecular weight (e.g. 1,000-10,000), and attached to the backbone of certain, if not all monomer units, a pyridyl group either directly bonded to the monomer or bonded to the repeating monomer unit through a linker.

The term "salt" is used herein in its conventional sense, to refer to ionic compounds that can result from the neutralization reaction of an acid and a base. They are composed of cations (positively charged ions) and anions (negative ions) so that the product is electrically neutral (without a net charge). These component ions can be inorganic such as chloride ($Cl^-$), as well as organic such as acetate ($CH_3COO^-$) and monatomic ions such as fluoride ($F^-$), as well as polyatomic ions such as sulfate ($SO_4^{2-}$). There are several varieties of salts. Salts that hydrolyze to produce hydroxide ions when dissolved in water are basic salts and salts that hydrolyze to produce hydronium ions in water are acid salts. Neutral salts are those that are neither acid nor basic salts. Zwitterions contain an anionic center and a cationic center in the same molecule but are not considered to be salts. Examples include amino acids, many metabolites, peptides and proteins. Molten salts and solutions containing dissolved salts (e.g. sodium chloride in water) are called electrolytes, as they are able to conduct electricity.

The term "polyacrylic acid" (PAA) means a polymer of acrylic acid units. The formula of PAA is $(C_3H_4O_2)_n$. The number of repeating units may be selected to yield a polymer with molecular weight e.g. from 2,000 to about 24,000. In a water solution at neutral pH, many of the side chains of PAA lose their protons and acquire a negative charge. This makes PAA a polyelectrolyte, and a weak acid cation.

The term "polysaccharide" means polymeric carbohydrate structures, formed of repeating units (either mono- or di-saccharides) joined together by glycosidic bonds. These structures are often linear, but may contain various degrees of branching. Polysaccharides are often quite heterogeneous, containing slight modifications of the repeating unit. Depending on the structure, these macromolecules can have distinct properties from their monosaccharide building blocks. When all the monosaccharides in a polysaccharide are the same type the polysaccharide is called a homopolysaccharide, but when more than one type of monosaccharide is present they are called heteropolysaccharides. Polysaccharides have a general formula of $C_x(H_2O)_y$ where x is usually a large number between 200 and 2500. Examples include, but are not limited to storage polysaccharides such as starch and glycogen; structural polysaccharides such as cellulose, chitin and arabinoxylans; bacterial polysaccharides like peptidoglycan. Other examples include pectin, carrageenan, alginates, chitosan, etc.

Ion binding polysaccharides are those such as the exemplified chitosan, xanthan, alginic acid, chitin, and pectin. An ion binding polysaccharide as described here works by chelation.

The term "chelation" is used in its conventional sense, to refer to the activity of a chelating agent. A chelate is a chemical compound composed of a metal ion and a chelating agent. A chelating agent is a substance whose molecules can form several bonds to a single metal ion. In other words, a chelating agent is a multidentate ligand. Chelants, according to ASTM-A-380, are "chemicals that form soluble, complex molecules with certain metal ions, inactivating the ions so that they cannot normally react with other elements or ions to produce precipitates or scale."

The term "chitosan" is used herein in its conventional sense, to refer to is a linear polysaccharide composed of randomly distributed β-(1-4)-linked D-glucosamine (deacetylated unit) and N-acetyl-D-glucosamine (acetylated unit). The amino group in chitosan has a pKa value of ~6.5, which leads to a protonation in acidic to neutral solution with a charge density dependent on pH and the % DD (degree of deacetylation) value. This makes chitosan water soluble and a bioadhesive which readily binds to negatively charged surfaces such as mucosal membranes. Chitosan enhances the transport of polar drugs across epithelial surfaces, and is biocompatible and biodegradable. Chitosan is produced commercially by deacetylation of chitin, which is the structural element in the exoskeleton of crustaceans (crabs, shrimp, etc.) and cell walls of fungi. The degree of deacetylation (% DD) can be determined by NMR spectroscopy, and the % DD in commercial chitosans is in the range 60-100%. On average, the molecular weight of commercially produced chitosan is between 3800 to 20,000 daltons. Chitosan has been described as a suitable biopolymer for the collection of metal ions since the amino groups and hydroxyl groups on the chitosan chain can act as chelation sites for metal ions. Further details on copper binding by chitosan may be found in Food Chemistry 114 (2009) 962-969. Chitosan has been described as a suitable biopolymer for the collection of metal ions since the amino groups and hydroxyl groups on the chitosan chain can act as chelation sites for metal ions. It has a structure illustrated, e.g. in US 2011/0136255.

The term "calmodulin" (an abbreviation for CALcium MODULated proteIN) is used herein in its conventional sense, refers to a calcium-binding protein expressed in all eukaryotic cells. It can bind to and regulate a number of different protein targets, thereby affecting many different cellular functions. Calmodulin undergoes a conformational change upon binding to calcium, which enables it to bind to specific proteins for a specific response. Calmodulin can bind up to four calcium ions, and can undergo post-translational modifications, such as phosphorylation, acetylation, methylation and proteolytic cleavage, each of which can potentially modulate its actions. Calmodulin is a small, acidic protein approximately 148 amino acids long (16706 Daltons) and, as such, is a favorite for testing protein simulation software. It contains four EF-hand "motifs", each of which binds a $Ca^{2+}$ ion. The protein has two approximately symmetrical domains, separated by a flexible "hinge" region. Calcium is bound via the use of the EF hand motif, which supplies an electronegative environment for ion coordination. After calcium binding, hydrophobic methyl groups from methionine residues become exposed on the protein via conformational change. This presents hydrophobic surfaces, which can in turn bind to Basic Amphiphilic Helices (BAA helices) on the target protein. These helices contain complementary hydrophobic regions.

Calmodulin is an exemplified ion binding protein that binds calcium. Other calcium binding proteins include troponin C and S100B. Other proteins that are not naturally metal ion binding proteins can be coupled to small molecule chelating agents. Other suitable ion binding proteins include CopA and metallothionein (binding copper), zinc finger proteins, cytidine deaminase, and nerve growth factor (binding zinc).

The term "boronic acid" is used herein in its conventional sense, to refer to an alkyl or aryl substituted boric acid containing a carbon-boron bond belonging to the larger class of organoboranes. Boronic acids act as Lewis acids. Their unique feature is that they are capable of forming reversible covalent complexes with sugars, amino acids, hydroxamic acids, etc. (molecules with vicinal, (1, 2) or occasionally (1, 3) substituted Lewis base donors (alcohol, amine, carboxylate)). The pKa of a boronic acid is ~9, but upon complexion in aqueous solutions, they form tetrahedral boronate complexes with pKa ~7. They are occasionally used in the area of molecular recognition to bind to saccharides for fluorescent detection or selective transport of saccharides across membranes. Boronate esters are esters formed between a boronic acid and an alcohol. Boronic acids have the formula $RB(OH)_2$, where R can be any group, e.g. alkyl. A boronate ester has the formula $RB(OR)_2$.

The covalent pair-wise interaction between boronic acids and 1,2- or 1,3-diols in aqueous systems is rapid and reversible. As such the equilibrium established between boronic acids and the hydroxyl groups present on saccharides can be employed to develop a range of sensors for saccharides. Potential applications for this interaction include systems to monitor diabetic blood glucose levels.

Boronic acids and boronic esters may be used to functionalize the nanopipettes embodied herein to be used in detecting saccharides including monosaccharides, disaccharides, oligosaccharides and polysaccharides, including glucose, a monosaccharide. Monosaccharides are the simplest carbohydrates in that they cannot be hydrolyzed to smaller carbohydrates. They are aldehydes or ketones with two or more hydroxyl groups. The general chemical formula of an unmodified monosaccharide is $(C.H_2O)_n$, literally a "carbon hydrate." Monosaccharides are important fuel molecules as well as building blocks for nucleic acids. The smallest monosaccharides, for which n=3, are dihydroxyacetone and D- and L-glyceraldehyde. Two joined monosaccharides are called a disaccharide and these are the simplest polysaccharides. Examples of disaccharides that could be sensed with a boronic acid coating include sucrose and lactose. Examples of analytes that are oligosaccharides include disaccharides, the trisaccharide raffinose and the tetrasaccharide stachyose. Examples of polysacchrides include starch, glycogen, chitin, cellulose, callose or laminarin, chrysolaminarin, xylan, arabinoxylan, mannan, fucoidan and galactomannan.

The term "saccharide binding protein" means a protein that specifically binds to a carbohydrate. The term "saccharides" is used synonymously with "carbohydrates". An example of carbohydrate binding proteins is the family of lectins. Examples include concanavalin, mannose-binding protein, peanut agglutinin, snowdrop lectin, ricin.

General Method and Apparatus

Described herein is a method and apparatus to control precipitation in aqueous solutions by voltage-directed ion migration, and to study the precipitation through its effect on ion currents through a nanopipette tip. Studying the earliest stage of precipitation at the nanoscale is technically challenging, but quite valuable as such phenomena reflect important processes such as crystallization and biomineralization. Using a quartz nanopipette as a nanoreactor, precipitation of an insoluble salt is induced to generate oscillating current blockades. The reversible process can be used to measure both kinetics of precipitation and relative size of the resulting nanoparticles.

FIG. 1 shows an example of an electrochemical setup according to the present invention measuring ion current oscillations through a quartz nanopipette 102, which has its tip in a solution 106 containing various ionic and/or carbohydrate species 112. Electronics are provided for measurement of ion current oscillations in the nanopipette. Ionic currents result from the flow of ions into or out of the nanopipette though the nanopore in response to a voltage differential between the inside and the outside of the nanopipette. The electronics include an electrode 104 in contact with the solution within the pipette; an amplifier 105 such as an Axopatch resistive feedback patch clamp and high speed current clamp amplifier, manufactured by Molecular Devices, with the negative input connected to the electrode 104; and a reference electrode 110 in the sample solution 106, outside the interior of the nanopipette. This exemplary setup measures ion current through a quartz nanopipette. Pore diameter at the tip is typically 40-60 nm. As exemplified below and shown here, solutions contain various ions such as KCl (0.1 M) and are buffered at pH 7, with 10 mM potassium phosphate in the barrel 102 and 10 mM Tris-HCl in the bath 104. Zinc chloride is included in the bath at concentrations of 2 to 20 μM. The use of a phosphate-free buffer in the bath is to prevent precipitation in the bath solution. As such, the precipitation is localized to the tip of the nanopipette when phosphate from inside the barrel mixes with zinc ions from the bath solution. Further details regarding the voltage clamp circuit may be found in U.S. Pat. No. 7,785,785, "Charge perturbation detection system for DNA and other molecules."

Figure 4:
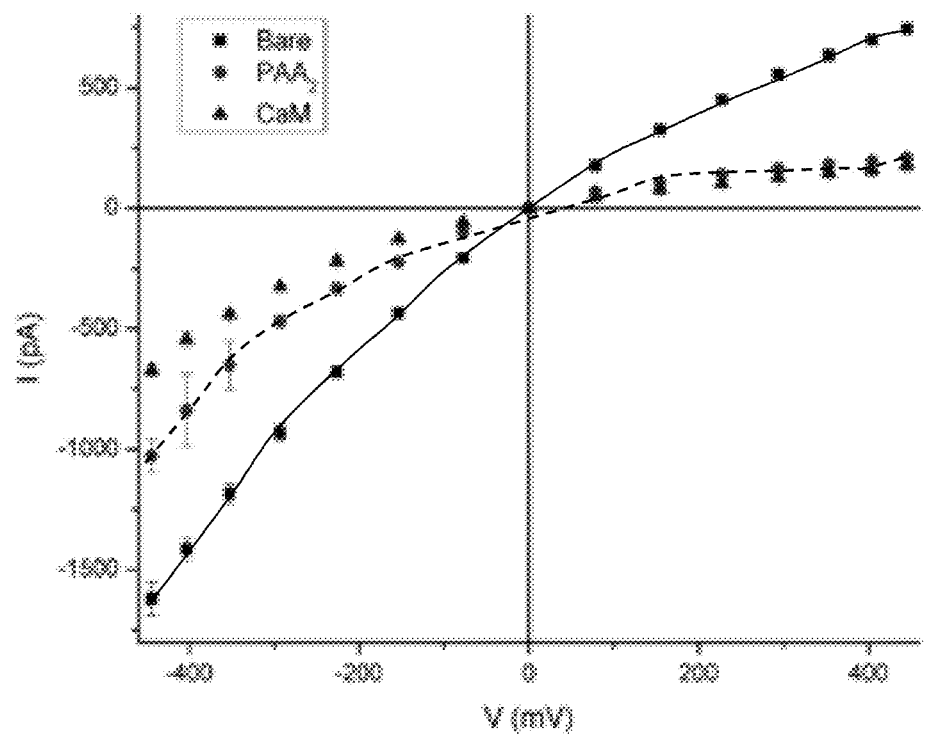
FIG. 4 is an IV plot showing data from an ion-binding surface modification (calmodulin/PAA/PLL) that would be applied as shown at 108 in FIG. 1, and shows ion sensitivity of the nanopipette biosensor. Solid line-bare pipette; dashed line-PAA2; triangles CaM.
Figure 9:
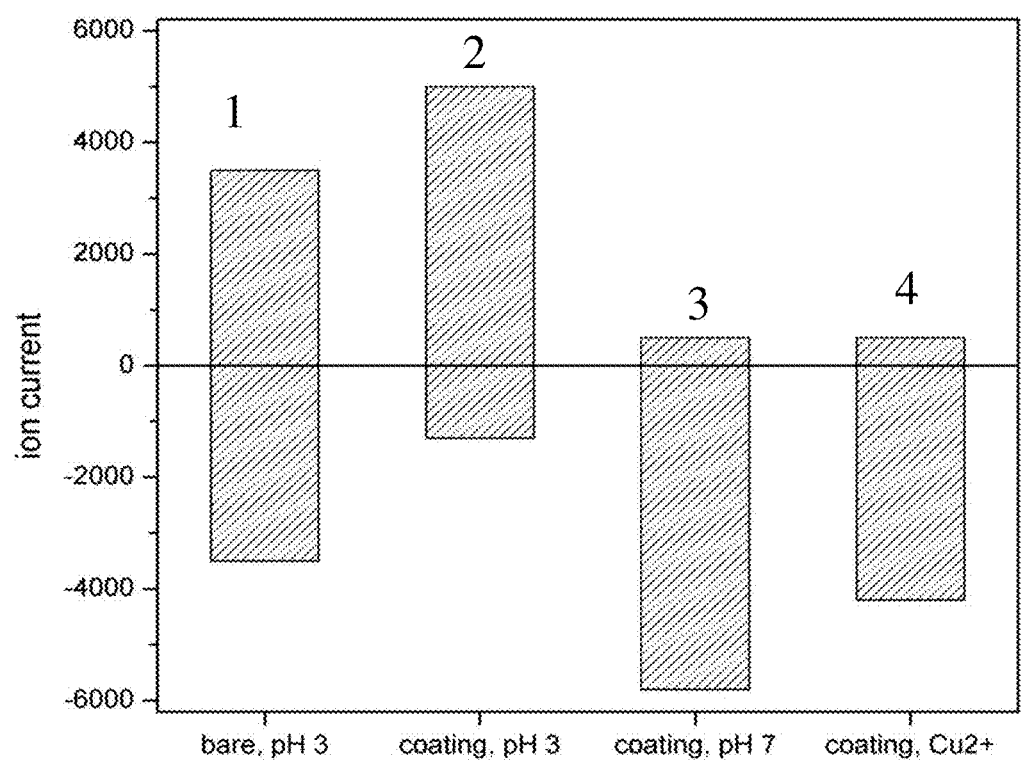
FIG. 9 is a graph that shows ion current under various conditions, indicating the effect of functionalization of a sensor with chitosan in 0.1M KCl, 10 mM phosphate buffer solution.

The same device in a different configuration can be used to measure ion current rectification as a means to detect metal ions, as illustrated e.g. in FIGS. 4 and 9. In this embodiment, a buffer such as pH 7 phosphate is as the electrolyte for both the barrel of the nanopipette and the bath solution. Also shown in FIG. 1 is a coating 108 on the inside bore, adjacent the nanopipette tip. This region is referred to as a "nanopore," and defines within it a "nanochannel." The coating 108 as further described below may extend in an a mesh-like structure across the tip, or may be a single coating on the interior surface, and may be used for specific binding of selected ions or carbohydrates. As described below, polyacrylic acid may be applied as shown at 108, i.e, applied to the silicate surface of the nanopipette and chitosan is applied on top of the polyacrylic acid. Cu ions are shown binding to the chitosan, but being released at pH 3.

Sensing metal ions by using a chelator differs from measuring changes in current oscillations due to nanoprecipitation at the nanopore. When the chelator binds catins, negative ionic current rectification indicates such binding, as described below.

The polymer is synthesized such that it is cationic, and the polymer, when embedded in the nanopore, displays positive current rectification. On binding saccharides, the positive charge is neutralized, and the ion current becomes negatively rectified. This is not the case for other systems in the literature in which boronic acid is attached directly to the glass. Those systems achieve modest changes in rectification (negative to slightly more negative) on sugar binding.

As is known, an I-V curve (current voltage curve) will exhibit various characteristics depending on the flow of charged ions through a nanopore. Where rectification takes place, the IV curve will not be linear, but will greater passage of current in response to a positive voltage (positive rectification) or in response to a negative voltage (negative rectification). The polarity of the voltage is given with reference to the electrode within the nanopipette. Thus, in operation, the present device will apply a number of voltage levels successively in the negative range, then in the positive range. For example, in FIG. 4, voltages of −400 mV to 0 and from 0 to +400 mV were applied in 14 discrete levels and currents measured at each level, in order to generate an I-V curve. This range may be narrowed when specific parameters of a given system are determined.

Figure 2:
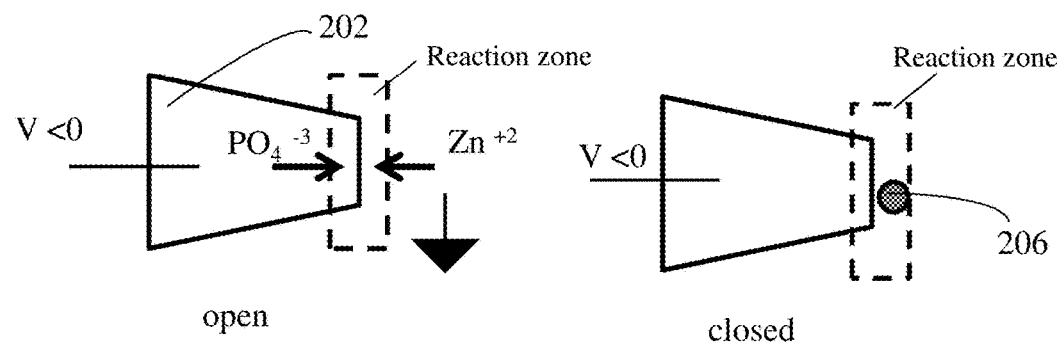
FIG. 2 is a schematic representation of an electrochemical set up as in FIG. 1, where formation of a precipitate at the nanopore causes a measurable blockage of ionic current.

FIG. 2 shows a configuration of a nanopipette circuitry and solutions causing ion current oscillations. A negative potential in the nanopipette barrel 202 (shown as V<0) draws zinc cations from the bath 106 (FIG. 1) into the pore, i.e. the opening of the nanopipette, while phosphate ions are pushed out of the nanopipette barrel 102 (FIG. 1). Mixing of the ions (anion mixing with cation) occurs in the nanopipette tip region 118. When a precipitate of sufficient size is formed, as shown at 206, the pore is blocked and ionic current decreases.

As described below, counter ions for the highly water insoluble salt zinc phosphate were separated by the pore of a nanopipette and a potential applied to cause ion migration to the interface. By analyzing the kinetic of the pore blockage, illustrated by a mass at 206, two distinct mechanisms were identified: a slower process due to precipitation from solution, and a faster process attributed to voltage-driven migration of a trapped precipitate. These techniques can be used to study precipitation dynamics and carry out measurement on trapped particles within a nanoreactor, which may be considered to be the "reaction zone" as shown in FIG. 2. In the example given, the particles are zinc phosphate salts. Other particles can include proteins, especially those that are charged, and the nanopipette can be used to test conditions for seeding crystals such as those used in crystallography. The device can also be used as an electrical sensor for either cations or anions based on nanoprecipitation with counter ions.

Also disclosed is an electrical sensor that reversibly binds ions using a nanopipette functionalized with receptors. Examples given are sensors for pH, calcium, copper, and carbohydrates. The receptor can be molecules with acidic or basic functionalities, metal chelators, or proteins. As a proof of concept for a calcium biosensor, the protein calmodulin was immobilized to the interior of a nanopipette tip. The sensor showed selectivity for calcium over magnesium in electrolytes of neutral pH, and the calcium signaling was reversible simply by immersing in fresh solution. This sensor was used for over 20 separate measurements with reproducible and concentration-dependent signals.

Furthermore, it was demonstrated that a nanopipette functionalized with certain polyelectrolytes reversibly bind transition metals. As a proof of concept, nanopipettes modified with chitosan as an external layer and polyacrylic acids (PAA) layered onto the quartz interior were shown to reversibly bind copper. In this case, chitosan/PAA is applied, as described below. The outside of the nanopipette is treated, e.g. with silane. The Cu ions bind to chitosan that is combined with the polyacrylic acid on the inner surface of the nanopipette. At pH 3, the Cu2+ ions come off of the chitosan. The surface treatment of the outside of the nanopipette may be carried out to facilitate penetration of the nanopipette through membranes, for example, lipid bilayers, cell membranes. The surface treatment of the outside of the nanopipette does not alter the binding of the receptors to the nanopipette.

Moreover, as shown below, the applied voltage can be employed to tune the binding properties of the nanopipette. In some embodiments, the nanopipette is functionalized with proteins to bind to ions, including to carbohydrates. In some other embodiments, the nanopipette is functionalized with boronic acids or boronic esters to detect carbohydrates. Additionally, sensors for pH were prepared by functionalizing the nanopipette with either polyelectrolytes containing amines or carboxylic acid groups, the amine-containing biopolymer chitosan, or an amino-silane. The pH sensors also showed rapidly reversible response to different buffers from pH 3 to pH 8. These types of sensors may be used for many different applications requiring a reversible and continuous sensor or array of sensors, such as monitoring of water quality, in-vivo single-cell assays, or functional ion mapping.

EXAMPLES

Example 1: Preparation and Characterization of Nanopipette Biosensors with PLL and PAA Polyelectrolyte Layers Quartz capillaries with filament (QF100-70-7.5) from Sutter (Novato, Calif.) were used as received and pulled with a Sutter P-2000 laser puller to give nanopipettes. Puller settings used were heat 620, filament 4, velocity 60, delay 170, pull 180. The settings are variable depending on the puller, and were adjusted as needed to provide nanopipettes showing negative ion current rectification with the desired conductance. The pipettes were backfilled with a buffered electrolyte (pH 7 Tris-HCI, 10 mM and KCI, 100 mM) unless otherwise indicated. The two sensors described are twin pipettes from one pulled capillary. Sensor CaM-1 was untreated prior to polyelectrolyte deposition, and CaM-2 was silanized with trimethylchlorosilane (TMCS) using vapor deposition. The nanopipette was placed in a sealed chamber of 0.5 L volume with approximately 0.1 mL of TMCS for 10 minutes. Both pipettes were then backfilled with buffered electrolyte and immersed in a bath of the same buffer. The ion current was measured with an Axopatch 700B amplifier (Axon) using Ag/AgCl electrode in the pipette barrel and a ground electrode in the bath. A sinusoidal potential from +500 mV to −500 mV (5 Hz) was applied to monitor the ion current during subsequent surface treatment. The polyelectrolytes poly-L-lysine PLL) and polyacrylic acid (PAA) were deposited on the surface of the nanopipette by sequential immersion of the pipette tip into buffered electrolyte containing either PLL or PAA at a concentration of 3 ppm, with immersion in buffer to wash after each polyelectrolyte deposition. A polyelectrolyte layer was determined to be stable if the resulting change in current rectification (positive for PLL, negative for PAA) was maintained during immersion in buffer. Both CaM-1 and CaM-2 were functionalized with four layers: PLL, PAA, PLL, and then PAA. The pipettes were then immersed in a solution containing 10 mg/mL each of NHS and EDC (100 mM pH 6.1 MES buffer, with 50 mM KCl) for one hour. Finally, the tips of the pipettes were washed and immersed in a solution of calmodulin (bovine brain, 0.05 mg/mL in pH 6.1 MES buffer (100 mM) with 50 mM KCl) and incubated for 18 h at 4° C.

The electrical properties of the sensors and response to metal salts were analyzed using the electrical setup described above. All measurements were carried out in pH 7-buffered electrolyte solution with aliquots of either calcium chloride or magnesium chloride (1 to 10 μL volumes) directly added to a bath of 0.3 mL buffer. Data was sampled at a rate of 200 Hz using the pClamp software and was processed using OriginPro 8.5. For continuous measurement data, the negative ion current peaks arising from the sinusoidal applied voltage were detected and plotted as a function of time. Line smoothing was done with a 50% percentile filter and a 10-point moving window, Current rectification coefficient (r) was calculated using the following equation:
$r = \log_{10} I_+ / I_-$
where $I_+$ is the magnitude of the ion current at a potential of 500 mV, and $I_-$ is the magnitude of the ion current at a potential of −500 mV. Errors in ion current reflect the standard deviation between three separate measurements of $I_+$ and $I_-$, with the same nanopipette after washing in buffer between measurements.

Example 2: Selective and Reversible Ca2+ Binding by Calmodulin Immobilized to a Nanopipette To achieve reversible and selective ion binding with a biological receptor, nanopipette sensors modified with calmodulin, a calcium binding protein that reversibly chelates calcium ($K_d \sim 10^{-6}$M) with high selectivity, were studied. Electrical sensors using immobilized calmodulin have been previously reported for probing both calcium concentration by Cui et al. in Science vol. 293: pages 1289-1292 in 2001 ("Nanowire nanosensors for highly sensitive and selective detection of biological and chemical species") and protein-protein interactions by Ivnitiski et ("An amperometric biosensor for real-time analysis of molecular recognition" *Bioelectrochem. Bioenerg.* 1998, 45(1), 27-32) and by Lin et al. ("Label-free detection of protein-protein interactions using a calmodulin-modified nanowire transistor" *Proc. Natl. Acad. Set U.S.A.* 2010, 107(3), 1047-1052). Our strategy took into consideration both immobilization of the protein to the pore, as well as the need to localize the receptor to the pore solution interface for rapid and reversible ion response.

In preliminary studies, the highest sensitivity to cations was observed with pores showing negative rectification, and our approach to surface functionalization ensured that the final sensor is based on such pores. Polyelectrolytes have strong electrostatic interactions with the charged pore surface, and the ion current rectification is an excellent indicator of polyelectrolyte binding to the nanopore. With this in mind, ion current measurements were used to monitor the layer-by-layer deposition of polyelectrolytes in the nanopipette and provide a negatively rectified nanopore with desired conductance. Amide bond formation between the amine groups in the protein and carboxylate groups on the outermost polyelectrolyte layer coupled the protein to the quartz surface. To localize the receptor to the pore-solution interface where there is greater interaction with the bulk solution, the pore was functionalized only by immersion, leaving the inside of the nanopipette filled with buffer. Because such an approach will functionalize a relatively large area of the surface in addition to the region directly around the pore, nanopipettes in which the external surface was coated with a hydrophobic silane was also tested.

The surface-treatment of the nanopipettes was monitored in real-time to determine stability of the surface chemistry for several steps. Twin nanopipettes, pulled from the same capillary, were taken through identical steps of surface treatment. The treatment involved reaction with pendant oxygen groups on the surface of the silica. PAA and PLL layers were applied, resulting in pendant carboxyl groups; calmodulin was bound to these groups. Thus surface functionalization on quartz was accomplished by deposition of polyelectrolyte layers (poly-L-lysine) PLL; (poly-acrylic acid) PAA, followed by amide bond formation to CaM (calmodulin) protein using NHS/EDC coupling. In effect, there is created a sandwich of quartz -PLL-PAA-PLL-PAA.

Figure 5A:
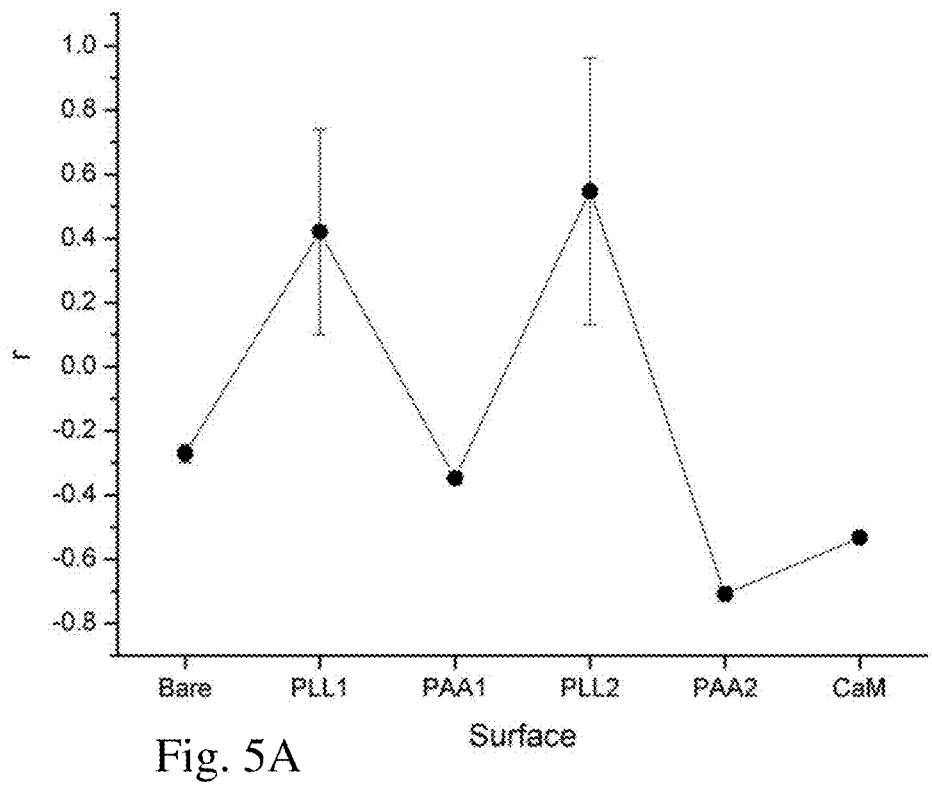
FIG. 5A is a graph that shows the rectification coefficient for surfaces of sensor CaM-1.
Figure 5B:
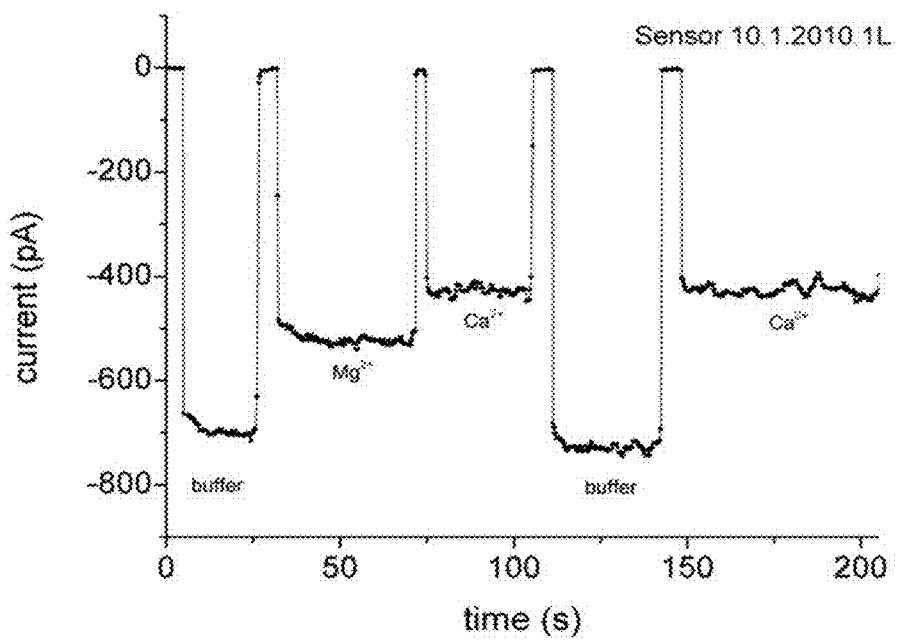
FIG. 5B is a current trace of the sensor of FIG. 5A.

Sensor CaM-1 was used directly after pulling, and CaM-2 was first treated with trimethylchlorosilane (TMCS) vapor to silanize the outer pipette tip. The ion current rectification (ICR) was monitored as the nanopipettes were immersed in neutral buffer containing either cationic poly-L-lysine (PLL) or anionic polyacrylic acid (PAA), with addition of subsequent layers only after the rectification remained stable in pure buffer. As shown by a current-voltage plot in FIG. 4, the bare nanopipette has a negative ICR, where current-voltage response of the bare pipette (■), after two layers of PLL and PAA (●), and after coupling with CaM (▲). After two layers of PLL/PAA, the current is still negatively rectified, but smaller in magnitude indicating a smaller pore after deposition. This behavior continues after immobilization of calmodulin protein, which is also negatively charged at neutral pH (pI~4). The rectification coefficient reflects the behavior seen in the current voltage curves: $r=-0.27\pm0.03$ (bare pipette), $-0.71\pm0.02$ (second layer of PLL/PAA), and $-0.533\pm0.014$ (CaM). The low error in these measurements demonstrates the stability of the surface at each step. The current rectification with the nanopipettes reflected the surface coating (see FIG. 5A, showing rectification coefficients that differ with different functionalizations). After applying PLL, the current rectification had a positive value, while after applying PAA, the rectification was negative. The current was measured with an oscillating sinusoidal potential (−500 to 500 mV, 5 Hz). Error bars reflect three separate measurements with the same nanopipette, with washing in buffer between each measurement. The CaM-modified nanopipette also showed negative current rectification, consistent with the overall negative charge of the protein resulting from carboxylate-containing residues. The current at a potential of −500 mV is strongly affected by the presence of calcium ions, as shown in FIG. 5B. The ion current is shown as a function of time in pH 7 buffer, with addition of 0.1 mM magnesium chloride, and in the presence of 0.1 mM calcium chloride. The selectivity for calcium is illustrated by the larger signal change for calcium ions relative to magnesium ions. The reversibility of the binding is shown by restoration of the signal by immersing in pure buffer, followed by calcium chloride.

Example 3: pH-Sensitive Nanopipette Sensors Functionalized with Metal Ion Binding Polymer (Chitosan Binding Cu)

Figure 6:
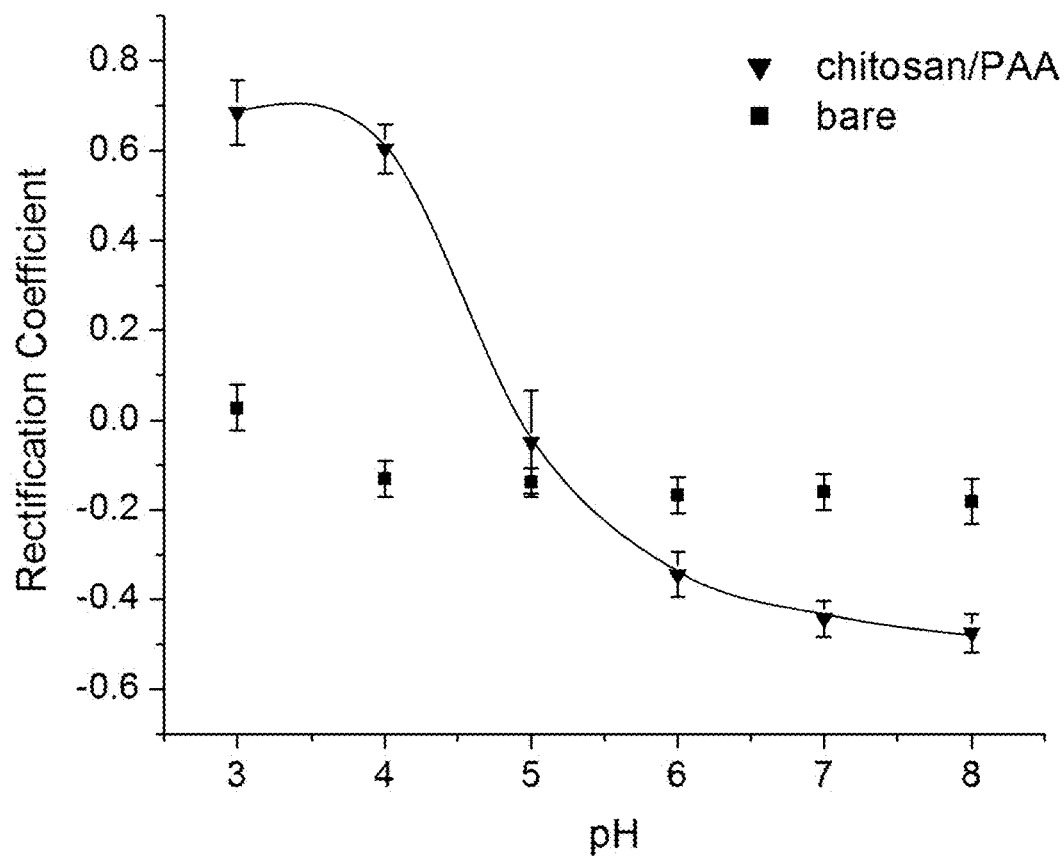
FIG. 6 is a graph that shows the pH response of a bare nanopipette (triangles) and chitosan/PAA improved nanopipette sensors (circles).

Sensors of pH were prepared by functionalizing the nanopipette with either an amino-silane, the amine-containing biopolymer chitosan (FIG. 6) or polyelectrolytes containing amines or carboxylic acid groups. The pH sensors showed rapidly reversible response to different buffers from pH 3 to pH 8. The nanopipette was filled with pH 7 electrolyte (100 mM KCl with 10 mM Tris-HCl buffer) and dipped in buffered electrolytes of varying pH (100 mM KCl with 10 mM phosphate/citrate buffer). Ion current was measured while applying a sinusoidal potential from −500 to 500 mV at 5 Hz. Measurements were carried out in a 0.1M KCl solution, buffered with 10 mM phosphate/citrate to the desired pH. Error bars were calculated from at least four different pH measurements with the same sensor (FIG. 6). FIG. 6 shows a comparison of the rectification coefficient for bare and chitosan/PAA-functionalized nanopipettes at different pH values. The rectification coefficient is more sensitive to pH for the functionalized nanopipette, owing to the protonable carboxylate and amine groups. At neutral pH, the functionalized nanopipette shows significantly more negative rectification than the bare nanopipette, showing that the coating results in more negatively charged groups at the surface of the nanopore.

Example 4: Electrostatic Physisorption of Polyelectrolytes and Chitosan on a Nanopipette Chitosan and polyacrylic acid were physisorbed using the following procedure: Nanopipette was immersed into 350 μL of a pH 3 buffered solution and 10 μL of the chitosan stock solution were added in the reservoir. The physisorption of chitosan should take place at acidic pH since this polyelectrolyte is not soluble in neutral pH. The nanopipette was then transferred into a 350 μL of a pH 7 buffered solution and 10 μL of the PAA stock solution was added in the reservoir. The functionalized nanopipettes were then cycled between the two solutions until the desired number of layers on the sensor was reached.

The conical geometry as well as the nanometer size pore generates an interesting electrochemical behavior on solid state nanopore. For instance, charged nanopores respond to a symmetric input voltage with an asymmetric current output, an effect referred to as current rectification. The origin of this effect in nanopipettes has been extensively described in a recent review published by two of the present inventors (Actis, P.; Mak, A.; Pourmand, N. *Bioanalytical Reviews* 2010, 1, 177.). Briefly, when the diffuse electrical double layer thickness is comparable with the pore size, the electrostatic interactions between fixed charged species on the nanopore surface and ionic species in solutions alters ion transport properties. In order to quantify the extent of the rectification, it has been introduced an useful parameter denoted as rectification coefficient or, in some cases, degree of rectification that is defined as the logarithm of the ratio between the current measured at particular positive voltage and the current measured at the same voltage but with the opposed polarity, i.e. $r = \text{Log}_{10} I+/I-$.

Quartz nanopores, being negatively charged, show a negative current rectification (r<0). The rectification can be inverted (r>0) by modifying the nanopore surface with charged functional layers such as poly-1-lysine, dendrimers, aminosilane, and chitosan.

Figure 7:
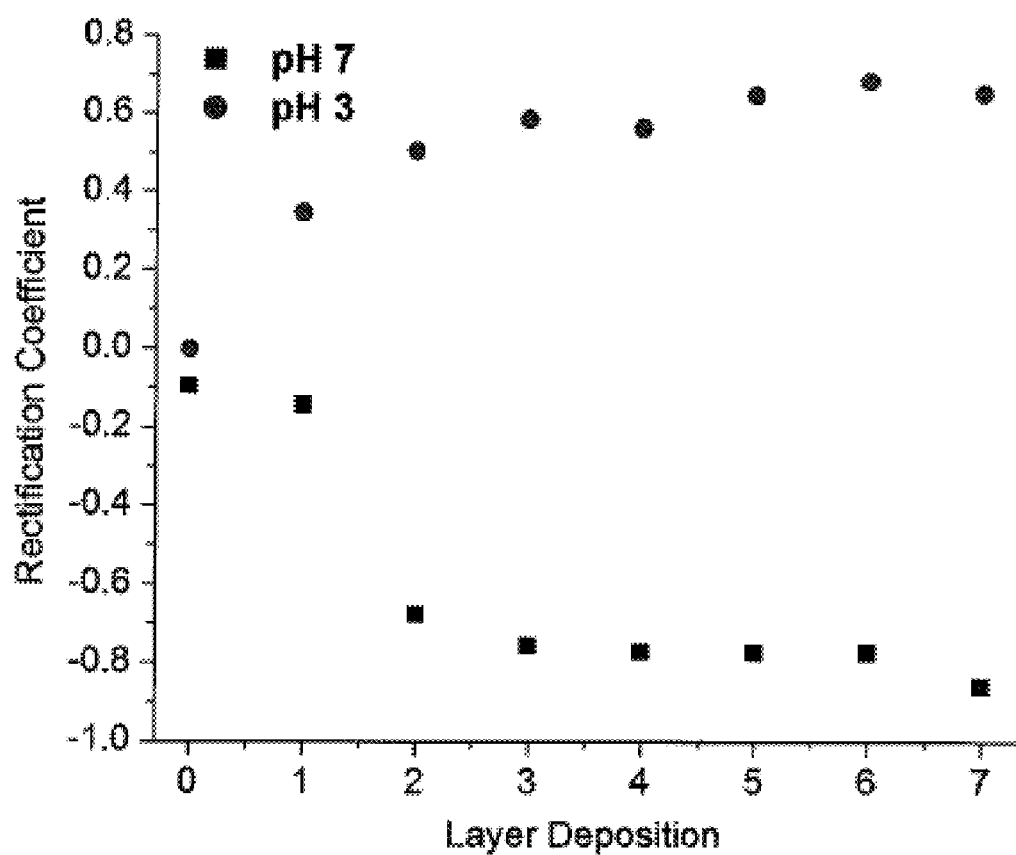
FIG. 7 is a graph showing variation of the rectification coefficient vs. numbers of chitosan/PAA layers deposited at pH 3 and 7.
Figure 8:
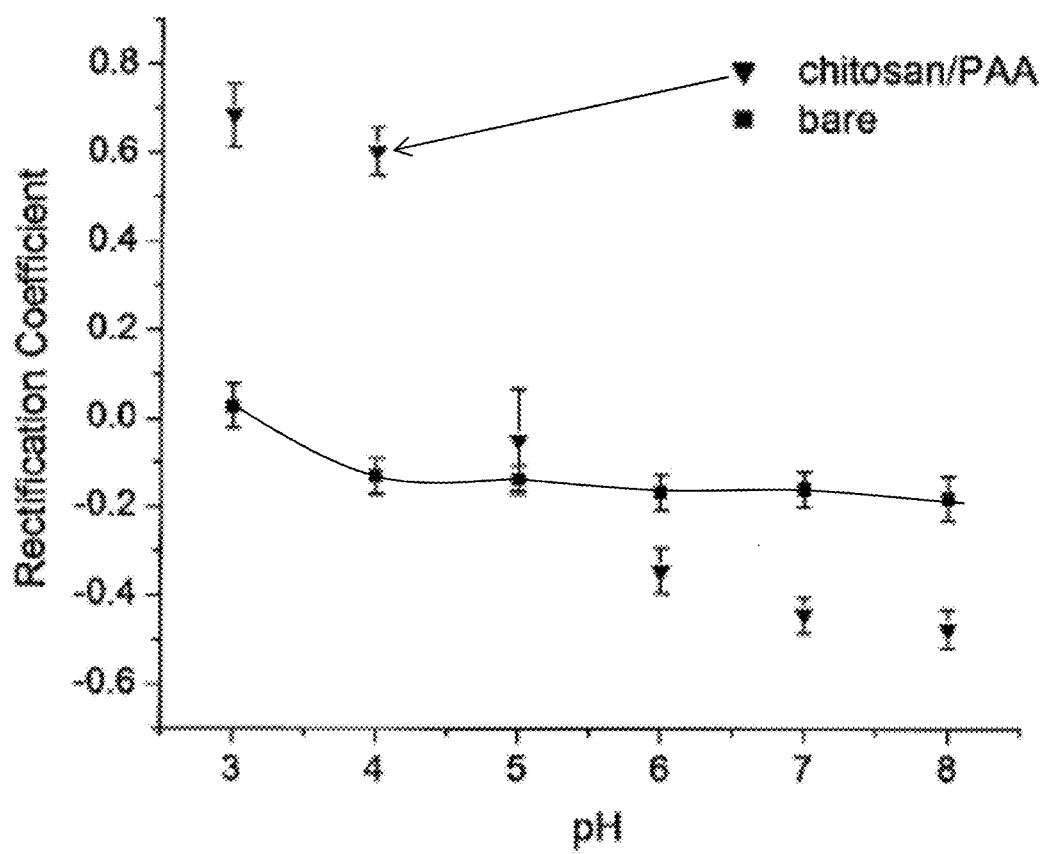
FIG. 8 is a graph that shows the pH response of a bare nanopipette (triangles) and chitosan/PAA sensor (circles).

The electrostatic physisorption of polyelectrolytes can be monitored by simple electrochemical measurements. The positively charged amino groups from the chitosan backbone allow the physisorption of the polyelectrolyte on the negatively charged nanopipette surface. Chitosan physisorption occurs at acidic pH only since this polysaccharide is insoluble at neutral pH. Similarly, carboxylic groups of polyacrylic acid (PAA) confer to the polymer a negative charge at neutral pH allowing the physisorption on the positively charged chitosan nanopipette. The deposition of every polyelectrolyte layer was monitored by electrochemical measurement. The rectification coefficient is an indication of the nanopipette surface charge. This parameter was employed to quantify the effect of the layer-by layer assembly on the quartz nanopipette. Interestingly, the multilayer assembly increased the rectification properties of the nanopipette: the rectification coefficient at pH increased from −0.1, for a bare nanopipette, to −0.8, after the physisorption of 5 layers of chitosan/PAA and plateaued afterwards. Similarly at pH 3 the rectification coefficient increased from 0 to 0.65 after 5 layers (FIG. 7). Besides the rectification coefficient, after 5 layers, there was no change in the overall current upon further additions of PAA or chitosan. This indicates that no polyelectrolyte was deposited on the sensor surface that was already fully covered with a chitosan PAA mixed layer. These results contrast with the ones described by Ali et al. (Ali, M.; Yameen, B.; Cervera, J.; Ramirez, P.; Neumann, R.; Ensinger, W.; Knoll, W.; Azzaroni, O. *Journal of the American Chemical Society* 2010, 132, 8338) that showed that the surface charge of a single asymmetric nanochannel in a PET membrane decreases dramatically with the number of layers assembled into it. This behavior can be explained by the imperfect multilayer formation that led to a mixed layer rather than a perfect layer by layer assembly. Therefore, the pH response of the chitosan/PAA modified nanopipette was studied to corroborate this assumption. Measurements were carried out in a 0.1M KCl solution, buffered with 10 mM phosphate/citrate to the desired pH. Error bars were calculated from at least four different pH measurements with the same sensor (FIG. 8). Chitosan has a $pK_a$ value of ~6.5, while PAA of 4.8. Assuming a perfect layer-by layer assembly, if PAA is the outermost layer, the nanopipette should be neutral at pH<4.8 and negatively charged at pH>4.8. Likewise, if chitosan is the outermost layer, the nanopipette should be positively charged at pH<6.5 and neutral charged above it. The rectification coefficient of the chitosan/PAA nanopipette, however, is positive at pH<5, and negative at pH>5. This indicates that at pH<5, the nanopipette permselectivity is governed by the protonated amino groups of chitosan while, at pH>5, by the negatively charged carboxylic groups of the PAA, thus demonstrating the mixed layer formation.

Example 5: Selective and Reversible Cu2+ Binding on Quartz Nanopipettes Electrostatically Modified with Chitosan and PAA Multilayers The physisorption of chitosan and PAA layers on a quartz nanopipette gives it reversible metal binding properties that are not observed with the bare sensor. Chelating properties of chitosan and PAA are well known and well described in the literature. Chitosan binds several metal ions; however it shows a stronger affinity for cupric ions. Thus it was decided, as a model system, to study the complexation of copper ions to chitosan/PAA sensors.

Reagents:

Chitosan was purchased from CERMAY. A stock solution of 5 mg/ml chitosan into pH 3 HCl solution was prepared and used for all the experiments described in this paper. Polyacrylic acid was purchased from Sigma Aldrich (Saint Louis, Mo.). PBS solutions at pH 7.4 were prepared using standard method. Aqueous reagents were prepared using ultrapure water with >18 MΩ cm$^{-1}$ resistance.

Sensor Fabrication:

Nanopipettes were fabricated from quartz capillaries with filaments, with an outer diameter of 1.0 mm and an inner diameter of 0.70 mm (QF100-70-5; Sutter Instrument Co.). The capillary was then pulled using a P-2000 laser puller (Sutter Instrument Co.) preprogrammed to fabricate nanopipettes with an inner diameter of 50 nm. Parameters used were: Heat 625, Fil 4, Vel 60, Del 150, and Pul 192. The resulting nanopipette tips had inner diameters ranging from 37 to 82 nn, with the mean diameter of 56 nm.

Measurement Setup:

All the measurements were performed in a two electrode setup since the current flowing through the nanopipette is too small to polarize a reference electrode. The sensor, acting as the working electrode, is backfilled with a 0.1M KCl, 10 mM Tris-HCl buffered at pH7, and a Ag/AgCl electrode is inserted. Another Ag/AgCl ground electrode is placed in bulk solution acting as auxiliary/reference electrode. Both electrodes are connected to the Axopatch 700B amplifier with the DigiData 1322A digitizer (Molecular Devices), and a PC equipped with pClamp 10 software (Molecular Devices). The system remained unstirred for the duration of the measurement, which was conducted at room temperature.

FIG. 9 shows the ion current at potentials of −500 and +500 mV for a bare nanopipette sensor and one that has been coated with PLL/PAA. The addition of Cu2+ in the reservoir immediately affects the permselectivity of the sensor causing a decrease in the ionic current at a potential of −500 mV. The binding is completely reversible and sensors are regenerated up to 5 times without any loss of performance.

Figure 10:
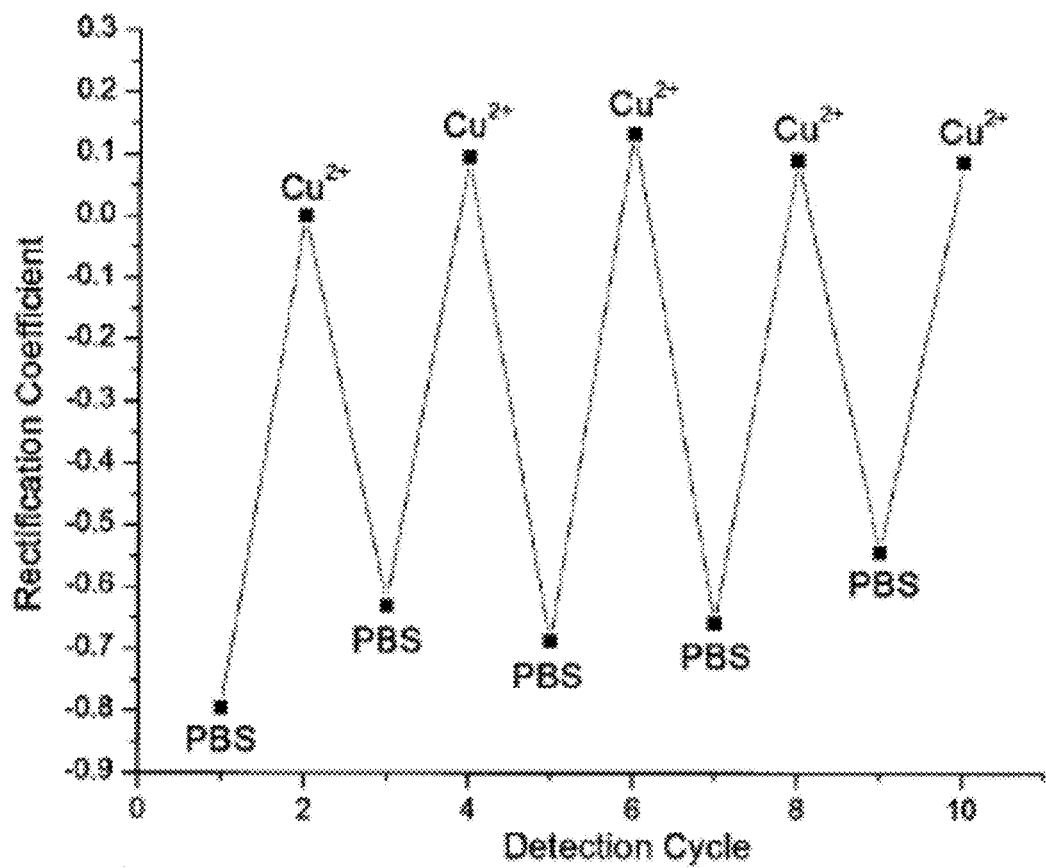
FIG. 10 is a graph showing variation of the rectification coefficient after recycling of the sensor. $Cu^{2+}$ concentration: 100 uM. The sensor was regenerated by immersing the sensor into a pH3 solution for 60 seconds.

Regeneration is performed by immersion of the sensor into a pH3 buffer for 60 seconds. Acidic pH protonates chitosan amino groups thus causing the release of the cupric ions in solution (FIG. 10). Alternative methods of regeneration such as immersion into citrate buffer at neutral pH and 0.1% EDTA showed equal success. It is important to consider the combined effect of both polyelectrolytes for the copper binding. Experiments were performed when the nanopipette was functionalized with chitosan and PAA only that showed little variation in the output current upon addition of copper in the bulk solutions. Furthermore, the interfaces between the polyelectrolytes and the quartz were not stable as the sensors were regenerated only once before a complete loss of the copper binding property. When mixed layers of chitosan and PAA were constructed on a nanopipette, the interface was stable over multiple detection cycles. Through FTIR measurements, Wang and coworkers demonstrated that —NH2, —OH and COOH groups were all involved in the copper adsorption by chitosan/PAA attapulgite composites (Wang, X.; Zheng, V.; Wang, A. Journal of Hazardous Materials 2009, 168: 970). It was speculated that a similar chelation mechanism takes place in the chitosan/PAA sensor enhancing the metal binding ability.

Figure 11:
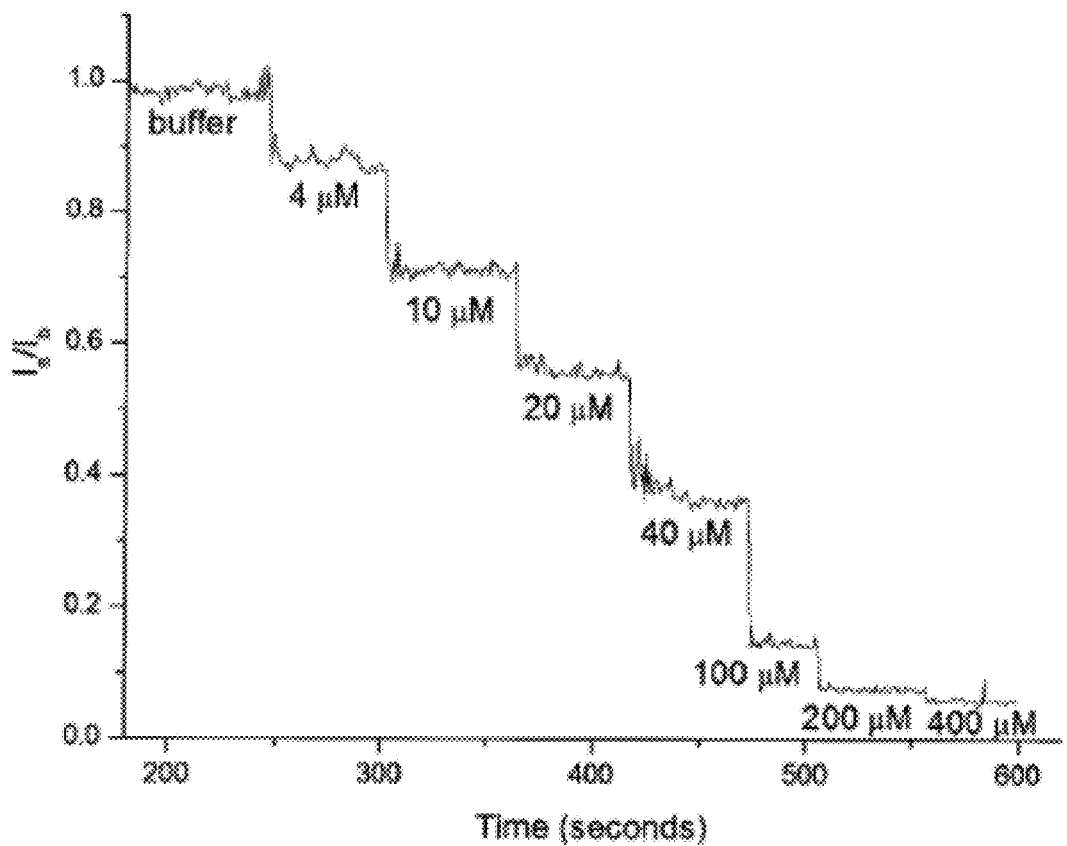
FIG. 11 is a trace that shows the response of the sensor to various concentrations of $Cu^{2+}$ in 0.1M KCl, 10 mM Tris-HCl, pH 7. A linear fit between $1/I_n$ and $1/C_{copper}$ (not shown) was calculated (R=0.997). Ion currents were determined at a potential of −500 mV applied to the electrode in the nanopipette barrel.
Figure 12:
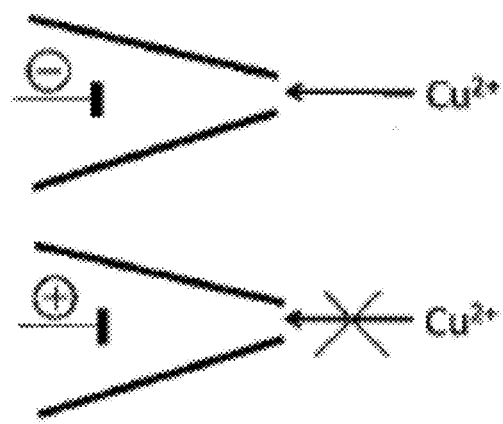
FIG. 12 is a cartoon depicting the role of electrophoresis on the interaction of cupric ions with a nanopipette.

The response of the sensor to different concentrations of copper ions was the investigated (FIG. 11). The sensor responds linearly to increasing $Cu^{2+}$ concentrations (FIG. 11, inset). The variation of the normalized current vs. $Cu^{2+}$ concentration is analogous to a Langmuir adsorption isotherm. The current was normalized according to:

$$I_n = 1 - \frac{I_s}{I_b}$$

Where $I_s$ is the signal after addition of copper ions in solution, and $I_b$ is the baseline signal measured in pure buffer. Assuming that the binding process is an equilibrium process, the variation of the normalized current is proportional to the number of cupric ions bound to the sensor, the binding sites are independent, and that the complexation equation is given by:

$$Cu^{2+}(aq) + Chitosan/PAA \leftrightarrow [Cu^{2+}-Chitosan/PAA]$$

One can estimate the thermodynamic affinity constant K for $Cu^{2+}$ binding to the sensor using the following equation:

$$\frac{1}{I_n} = \frac{1}{I_{max}} + \frac{1}{I_{max} K c_{Cu^{2+}}}$$

Where $I_{max}$ is the $I_n$ value at maximal surface coverage, and c is the concentration of cupric ions in solution. From the linear fit of FIG. 11, a K value of $4 \times 10^4$ $M^{-1}$ can be extrapolated. This value is in good agreement with the ones calculated for cation adsorption to chitosan with different platforms.

Example 6: Influence of the Waveform, Amplitude and Frequency of the Applied Voltage The applied voltage, i.e. the voltage between an electrode containing the solution inside of the nanopipette and an electrode in the external solution, plays a crucial role in the detection mechanism. Molecules can be trapped or concentrated at the tip of a nanopipette. Furthermore, the applied voltage increases the probability of a binding event inside the sensing region of the sensor. First, how the amplitude and the frequency of a sinusoidal waveform affect the nanopipette electrical single upon binding of copper ions was studied Response of the sensor to a fixed concentration of Cu2+ (20 uM) as a function of the (a) amplitude and (b) frequency of the applied voltage was measured in a bath solution: 0.1M KCl, 10 mM Tris-HCl, pH 7.

A higher voltage applied gave a larger change in the output current upon chelation of cupric ions by the chitosan/PAA sensor. For an equal copper concentration (20 μM), the current decreased to 5% of its initial value at 1 V amplitude while only 46% decrease was detected with 50 mV applied.

Interestingly, the higher the frequency of the applied sinusoidal voltage the smaller was the change measured upon binding of copper by the sensor. For a 20 μM $Cu^{2+}$ concentration in the bulk solution, the current decreased to 68% of its initial value at 1 KHz frequency while to 58% at 0.5 Hz.

Figure 13:
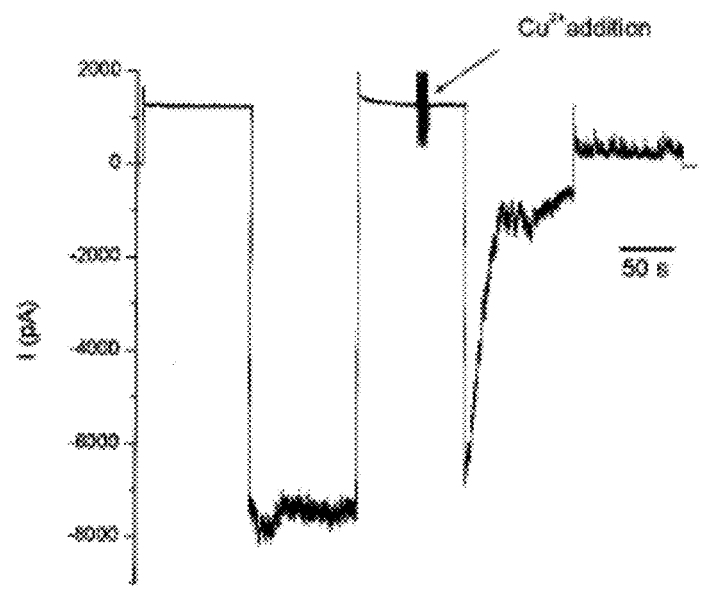
FIG. 13 is a trace showing output current, the arrow indicates the addition of $Cu^{2+}$ ions (final concentration in solution 150 uM). No change is detected while applying a positive voltage while an immediate response occurs upon switching to a negative potential that causes a variation on the following positive step.

Once characterized the response of the sensor to an AC voltage, the effect of a DC voltage was investigated. The binding of copper on the sensor can be controlled by the applied voltage. When a positive voltage is applied, cations are depleted from the nanopipette tip due to the electrophoretic flow. Leveraging this effect the binding of copper on the sensor can be triggered by controlling the applied voltage. Upon a positively applied voltage no binding occurs as cupric ions are depleted from the nanopipette tip, as soon as the voltage is switched to negative, binding occurs causing a decrease in the ion flow, a change that is reflected on the next positive step (FIG. 13).

Example 7: Voltage-Gated Nanoreactor for Detection of Precipitation with Nanopipette This example discloses how a voltage bias across a nanopipette opening can be employed to control ion migration and cause precipitation of an insoluble salt at the interface of two aqueous media. Furthermore, the conditions required for generating oscillating current due to zinc phosphate precipitation in a nanopore, as well as investigations into the nature of the precipitate and its subsequent evacuation from the pore are described. Further it is shown that a pore which appears permanently blocked by precipitation can be briefly cleared with a voltage pulse, and the method is used to examine the kinetics of pore blockage.

Reagents and Solutions

Stock solutions of metal salts (100 to 500 mM) were prepared in Milli-Q ultrapure water with 5% HCl. These were then diluted in buffer the day of the experiment. Calcium chloride tetrahydrate was purchased from Fisher. Zinc chloride, iron(III) chloride, and magnesium chloride (1.00 M solution) were purchased from Sigma-Aldrich. Buffer solutions were prepared from potassium chloride (Baker), sodium phosphate, dibasic (Sigma), and TRIS-HCl (1 M solution, pH 7.00, Sigma) and adjusted with either HCl (1 M) or KOH (0.1 M). All buffer solutions used for analysis contained 10 mM buffer and 100 mM potassium chloride.

Quartz Nanopipette Fabrication

Nanopipettes were fabricated from quartz capillaries with filaments, with an outer diameter of 1.0 mm and an inner diameter of 0.70 mm (QF100-70-5; Suffer Instrument Co.). The capillary was then pulled using a P-2000 laser puller (Suffer Instrument Co.) preprogrammed to fabricate nanopipettes with an inner diameter of approximately 50 nm. Parameters used were: Heat 625, Filament 4, Velocity 60, Delay 170, and Pull 180. In a solution of 10 mM buffer and 100 mM KCl, the pipettes gave a current between −2500 and −4000 pA at a potential of −0.5 V.

Measurement Setup

For measuring ionic current through a nanopipette, a two electrode setup was used. The nanopipette was backfilled with buffer solution and an Ag/AgCl electrode inserted. Another Ag/AgCl electrode was placed in 0.3 mL bulk solution acting as auxiliary/reference electrode. Both electrodes were connected to an Axopatch 700B amplifier with the DigiData 1322A digitizer (Molecular Devices), and a PC equipped with pClamp 10 software (Molecular Devices). Positive potential refers to anodic potential applied to the electrode in the barrel of the pipette relative to the counter electrode. Experiments were carried out at 24° C.

Voltage-Driven Nanoprecipitation

To induce zinc phosphate precipitation by voltage-driven mixing, the barrel of a nanopipette was backfilled with a solution of phosphate buffered electrolyte, arid the tip immersed in a phosphate-free Tris-HCl buffer. An aliquot of zinc chloride solution was added to the bath and stirred by repeated pipetting. The system was monitored while applying voltages from +500 to −800 mV. Experiments at different pH varied the phosphate buffer in the barrel only, with pH values of 6, 7, 8, or 10.

Kinetics of Current Oscillations

Nanopipettes were selected with a current value of −3500 to −4500 pA at a potential of −500 mV. Potentials from −300 to −500 mV produced current oscillations, for which a threshold was set for high and low conductance states. By measuring the time from high to low conductance, the slope of pore closing was estimated in pA per ms. The high and low conductance states were set as follows: −500 mV, −1700 and −1200 pa; −400 mV, −1200 and −700 pA; −350 mV, −900 and −400 pA; −300 mV, −1000 and −500 pA. For temporary opening of the pore, a biphasic waveform was used, where the applied potential oscillated between +500 and −500 mV for a period of 2.5 s each. The threshold for high conductance was set at −3500 pA, and the low conductance state at −2000 pA. The slope was calculated from the time required to reach the low conductance state.

Data Analysis

Data was sampled at a rate of 1 kHz using Clampex software. Data processing was done using Clampfit and OriginPro 8.5 (OriginLab, Northhampton, Mass.). Calculation of relative time in high vs. low conductance states used the peak finding function of OriginPro to find either negative (high conductance) or positive (low conductance) peaks, and the number of events in each state calculated as a percentage of the total events.

Results

To use the nanopipette as a nanoreactor, conditions to control the precipitation of zinc phosphate at the pore through ion migration was established. In a typical setup, an Ag/AgCl electrode is inserted into an electrolyte solution (100 mM KCl with 10 mM buffer) that fills the barrel of a nanopipette. The pipette tip is immersed in an electrolyte bath, which also contains an Ag/AgCl ground electrode (see FIG. 1).

Figure 3:
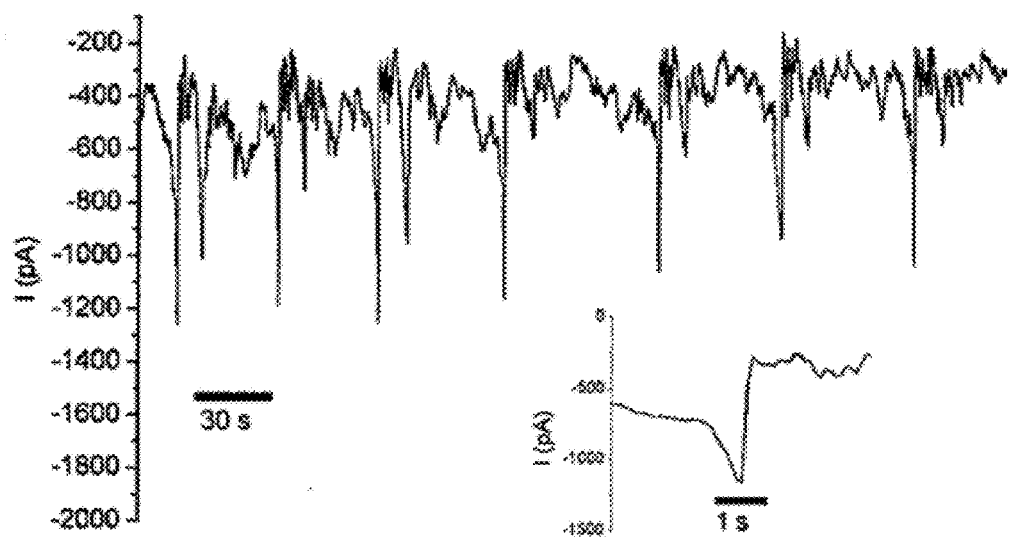
FIG. 3 is a graph that shows current oscillations in a nanopipette setup used for measuring precipitation, with 2 micromolar zinc chloride in the bath and a potential of −350 mV. Inset: expanded view of one of the open states.

On applying a potential, a steady ion current is measured. However, on adding micromolar concentrations of zinc chloride to the bath, the system undergoes oscillating periods of high and low conductance. These cycles were attributed to precipitation of highly insoluble zinc phosphate inside the nanopipette tip, and its subsequent evacuation from the pore. The oscillations caused by nanoprecipitation in such pipettes are on the order of seconds, as shown in FIG. 3, and are marked by a fluctuating state of low conductance and rapid, short-lived oscillations to a state of high conductance. The time plot of (FIG. 3) of the ion current at −350 mV potential shows several precipitation events that do not terminate with complete opening of the pore; rather, there are many events in which the low-conductance state fluctuates between −400 and −700 pA. These are likely due to precipitates that are evacuated before they grow to a size sufficient to completely block the pore. When a state of high conductance is reached, however, the current consistently reaches a maximum value of roughly −1200 pA followed by a rapid drop to −400 pA. This indicates a complete clearing of the pore followed by rapid precipitation.

To show that the precipitation reaction is controlled by the voltage-induced ion migration of zinc and phosphate ions, and does not simply occur by mixing at the nanopore, which is the interface of the two solutions, the zinc and phosphate counter ions were isolated in two separate solutions; phosphate ions are confined to the inside of the nanopipette, and zinc ions are in the bath (FIG. 1), The minimum required voltage to induce oscillating current blockage in this system is −300 mV. At potentials from +500 mV to −200 mV, a stable current is seen. At −300 mV, the current immediately becomes blocked with rapid fluctuations. The existence of a voltage threshold for the nanoprecipitation reaction indicates there is little mixing between the two counter-ions at the interface of the two solutions. Applying a positive potential gives a signal of smaller magnitude due to current rectification, but the signal is not influenced by the presence of zinc or phosphate salts. This voltage-dependent effect is consistent with the movement of ions toward the electrode of opposite charge, with phosphate and zinc ions meeting at the pipette tip (FIG. 2). When the placement of solutions is reversed such that zinc chloride is inside the pipette barrel and phosphate is in the bath, no blockage occurs with either a positive potential or a negative potential. While a positive potential in this configuration can in theory cause precipitation as zinc ions are pushed out of the pipette and phosphate migrates into the pore from the bath, this is not observed. The lack of current blockage in this configuration may be due to exclusion of cations (such as zinc) at the inner tip of the pipette, a phenomenon often cited as a cause of current rectification in conical nanopores.

Further investigation was conducted on the nature of the precipitate by varying the pH and the concentration and composition of the ions in the bath. It was assumed that the precipitate is composed of zinc phosphate, a salt which is highly insoluble in aqueous systems with $K_{sp}$ of $10^{-35}$ (mol·L$^{-1}$). While the predominant species in solution at pH 7 are dihydrogen phosphate ($H_2PO_4^-$) and hydrogen phosphate ($HPO_4^{2-}$), zinc phosphate is thermodynamically stable and forms in solutions at neutral or acidic pH. A solution is saturated with roughly $1 \times 10^{-7}$ M phosphate and zinc ions. Oscillating current behavior was seen in pipettes filled with phosphate buffer from pH 6 to pH 10, and with zinc chloride added to the bath at concentrations between 2 and 40 μM. While other divalent ions such as calcium and magnesium were tested at those concentrations, the only other comparable blockage was with iron(III) chloride (10 μM), which irreversibly blocked the pore. This is likely due to iron(III) hydroxide precipitation, a salt even less soluble than zinc phosphate ($K_{sp}$ Fe(OH)$_3$ $10^{-39}$).

Figure 14:
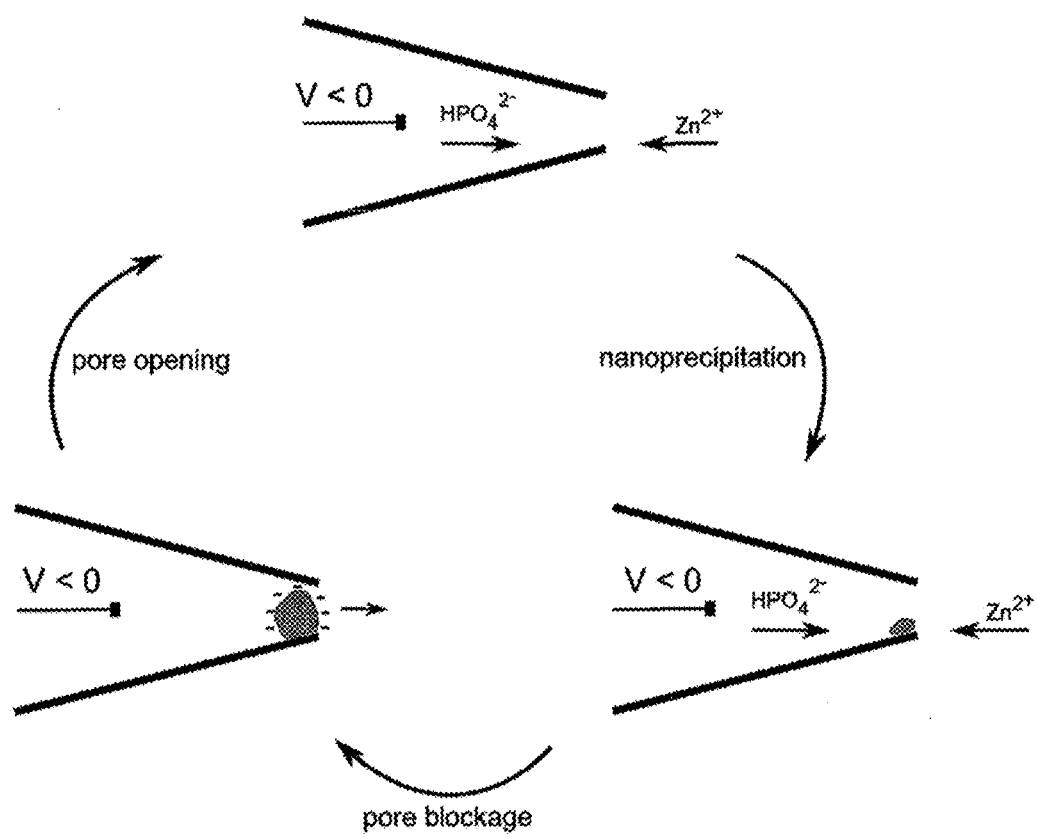
FIG. 14 is a cartoon illustration of oscillations in ion current by clearing of a precipitate from a nanopore at a tip of a nanopipette.

There are several possible mechanisms by which a nanopore blocked by precipitation spontaneously becomes cleared. For current oscillations seen with phosphate salts of calcium and cobalt in PET track-etched nanopores, the precipitation was attributed to voltage-induced concentration of salts in an asymmetric nanopore, causing a local increase in salt concentration to supersaturation levels. This led to a hypothesis in which the precipitate rapidly dissolves due to ion depletion in the nanopore. A computational study supported a second mechanism, wherein protons donated by hydrogen phosphates in the precipitate are accepted by oxides at the pore surface, weakening the pore-particle interaction and allowing the particle to clear by migration. For the pore blockage reported here, the effect is only observed at concentrations between 1 and 100 micromolar zinc chloride, well above the saturation level for zinc phosphate. Thus, the latter mechanism offers an explanation for the oscillations observed here. To support this mechanism, current oscillations were induced in a pipette filled with phosphate buffer and immersed in a saturated solution of zinc phosphate. The precipitate in such a case is likely ejected from the pore, rather than dissolved (see FIG. 14). With a negative potential, shown in FIG. 14 as V<0 in the bore, oppositely charged ions migrate to the interface of the solutions inside and outside the pipette. Zinc phosphate precipitates at the pore, causing ion current to decrease. When the precipitate has grown to sufficient size, it is cleared from the pore by electrophoretic forces.

If the zinc phosphate precipitate migrates out from the pore as believed, it remains to be explained why current oscillations are seen only with negative potentials. While the exact chemical composition of the precipitate is unknown at this time, clusters of zinc phosphate have been shown to have a net negative charge at neutral pH, as measured by zeta potential. Precipitation and blocking of the pore will lead to an increased electric field at the pore, and thus a negative potential may move the precipitate out of the pore and into the bath by electrophoretic and electroosmotic forces. While the applied voltages are low in these experiments (−300 to −500 mV), the voltage drop will be greatest across the region of highest impedance, such as the blocked pore. Ejection of the particle by electrophoretic forces may also help to explain why iron(III)hydroxide does not exhibit spontaneous clearing from the pore, as the particles carry a positive charge and would be expected to have a strong interaction with the negatively charged quartz surface. Interestingly, a pipette showing positive current rectification after deposition of a poly-L-lysine electrolyte layer became blocked from voltage-induced mixing of zinc phosphate, but did not display any oscillations to an open state. Presumably, the negatively charged precipitate has a high affinity for a positively charged pore and cannot be dislodged as easily.

Figure 15A:
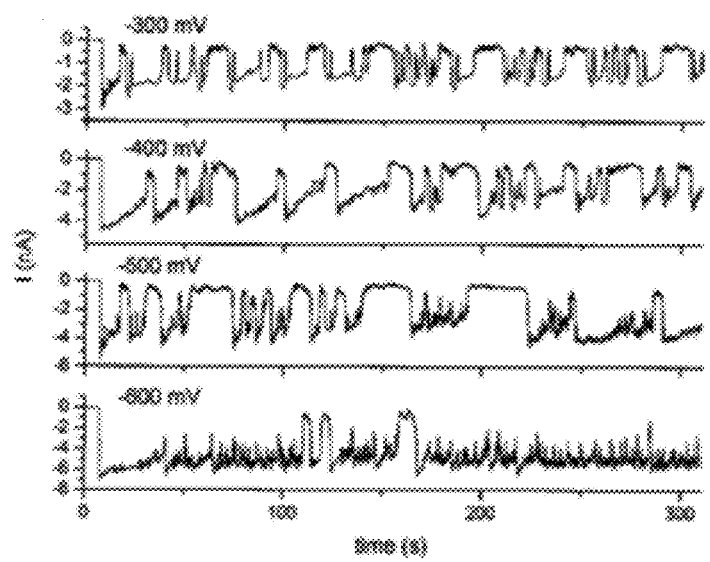
FIG. 15A is a graph of oscillations on applying a negative potential to a pipette filled with phosphate buffer (pH 7) and immersed in a bath of Tris-HCl buffer (pH 7) with 2 micromolar zinc chloride.
Figure 15B:
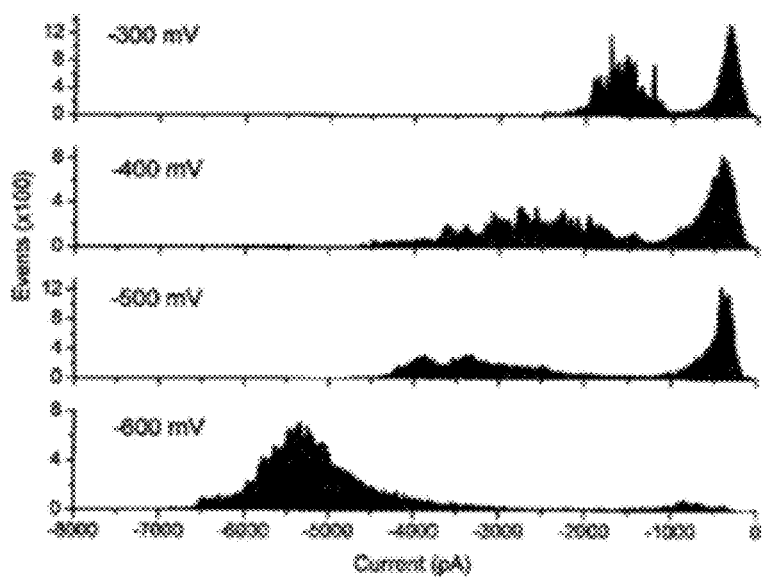
FIG. 15B is a histogram showing events from FIG. 15A in the states of high and low conductance.

In addition to initiating the process of nanoprecipitation with the voltage-controlled nanoreactor, the size of the precipitate may also be controlled. If the pore is cleared due to electrical forces at the tip of the nanopipette, then increasing the potential is expected to eject smaller particles that have not completely blocked the pore. This was demonstrated experimentally on reaching a potential of −600 mV, where two distinct low-conductance states are seen (FIG. 15).

A histogram showing counts for different current levels shows a state of high and low conductance for −300, −400, −500, and −600 mV. At −600 mV, there is clearly more time spent in the open state relative to the closed state, also visible in the time plot (FIG. 15A). For example, the system at −300 mV shows 41% time spent in a high conductance state, while at −600 mV, that value is 73%. This indicates that as the potential increases, the precipitate is prevented from blocking the pore. Unlike the other voltages measured, the time plot at −600 mV shows three states: a low conductance state (−800 pA) that occurs infrequently and for longer duration than an intermediate state (−3000 to −3500 pA), and a high conductance state (−6000 pA). It is believed that the intermediate state corresponds to precipitates that are ejected after only partially blocking the pore. At voltages less than −600 mV, the precipitate is cleared only after it has grown to sufficient size to completely block the pore.

It is expected that at some point salt will accumulate in the pore to an extent that the precipitate cannot be ejected. This stage of precipitation was also studied with the nanoreactor, and revealed an unforeseen phenomenon. Many of the nanopipettes underwent three stages of blocking by nanoprecipitation. The first stage was that of spontaneous current oscillations with a constant negative applied potential. After a period of 20 minutes or more, the pore became blocked and exhibited a steady state of low-conductance. At this stage, however, the pore could be temporarily forced into a high-conductance state by a rapid pulse of positive potential. Finally, the pipette would become irreversibly blocked. For the first two stages, the goal was to understand what was occurring in the pipette as the pores are becoming cleared and subsequently blocked. The kinetics of pore opening cannot be compared for the two systems, as they occur under potentials of opposite polarity. The kinetics of pore closing was investigated to find if there are different mechanisms at work for a pipette in the two stages described.

If the pore can be cleared by a negative potential causing migration of a negatively charged particle out through the nanopore, then a positive potential is expected to move the precipitate in the opposite direction, to the broader shaft of the pipette tip. For blocked pores, a pulse of +500 mV was briefly applied (0.2 to 2 s), followed by reversal of the voltage to −500 mV. At the negative voltage, a high conductance state is seen from the previously blocked pore, which again becomes rapidly blocked (data not shown). The brief open state is of the same magnitude as the open states in pipettes undergoing current oscillations, and is therefore attributed to an open pore rather than a transient current due to the rapid change in voltage. The temporary high-conductance state indicates that the precipitate has migrated away from the pipette tip and is either replaced by precipitation from solution, or that the particle is moved back toward the pore when the potential is reversed from positive to negative.

The kinetics of pore closing will be distinct for the two different mechanisms, nanoprecipitation vs. migration of a particle into the pore. To compare blocking kinetics in oscillating vs. blocked pores, the rate of current blockage for individual events at −500 mV for both conditions was quantified. For blocked pores that have been briefly opened with a +500 mV pulse, the current at a blocking event decreases with a slope of 74±13 pA/ms, as compared to 4±2 pA/ms for a pore undergoing current oscillations. The significantly faster current blockage indicates a blocking mechanism other than nanoprecipitation from solution. Rather, this may represent voltage-driven shuttling inside the nanopipette, from base to tip, of a particle too large to exit through the nanopore. This phenomenon has thus far only been observed with zinc phosphate salts, and did not occur with blockage from other precipitates such as iron (III) hydroxide.

If the precipitate in a blocked nanopipette is indeed moved within the tip during pulses of positive potential, then the particle can be trapped with alternating voltages to leave the pore unblocked. By applying sinusoidal potentials of sufficiently high frequency, an "open" current can be produced from pipettes which appear to be blocked by zinc phosphate. For measurement, a pipette filled with pH 7 phosphate buffer (10 mM with 100 mM KCl) was immersed into a bath of pH 7 Tris buffer (10 mM with 100 mM KCl) containing 2 µM zinc chloride. The pipette became blocked after constant potential of −500 mV for several minutes, and sinusoidal potential from 500 to −500 mV was applied at frequencies of 0.1, 0.5, 1, and 5 Hz. At lower frequencies such as 0.1 Hz, the pore can be seen to briefly approach a high-conductance state before becoming blocked as the potential oscillates to a negative voltage. At higher frequencies, a much higher conductance state is achieved, and the pore is cleared by a positive potential before it becomes blocked.

The high-conductance state achieved with higher frequencies of sinusoidal voltage represents trapping in space of a nanoprecipitate using an oscillating electric field, and also allows the magnitude of current to be precisely controlled with frequency of the applied potential.

Example 8: Carbohydrate (Saccharide)-Responsive Functionalized Polymer Coating

Figure 17:
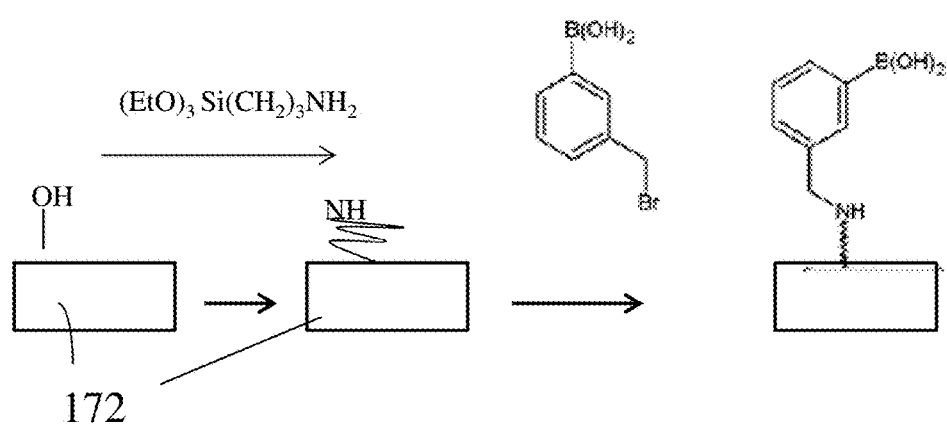
FIG. 17 is a schematic showing direct two-step functionalization of a quartz surface 172 with a boronic acid.
Figure 18A:
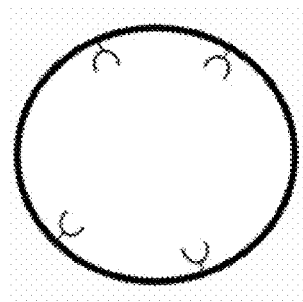
FIGS. 18A, 18B and 18C is a series of drawings showing an end view of a nanopore and illustrating three methods for immobilization of receptors to a nanopore.
Figure 18B:
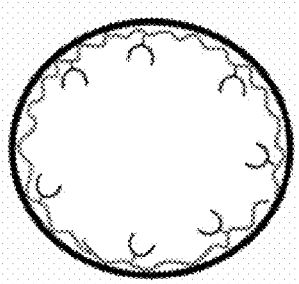
Figure 18C:
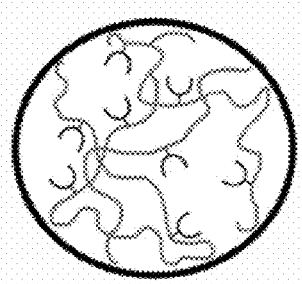

Nanopipette sensors were developed for sensing saccharides in a sample solution using boronic acid chemistry applied to the nanopore channel. The rationale is that while saccharides may be small relative to the pore (which may be e.g. 10-40 nm in opening diameter), the binding of saccharides to boronic acids can cause the neutral boronic acid to convert to the negatively charged boronate. Nanopipettes and other conical nanopores exhibit current rectification, or ion perselectivity, which is sensitive to surface charge. Initial attempts to make reversible sensors based on the known methods of surface modification—either through covalent attachment of boronic acids (a schematic of which is illustrated in FIG. 17) or deposition of a functionalized polyelectrolyte—resulted in sensors that were either not sufficiently sensitive or responded irreversibly. In a nanopipette covalently modified as shown in FIG. 17, the ion current responded to 3 mM glucose in pH 7 buffer. It was reasoned that the sensitivity of the nanopore would be increased if the recognition element covered the entire cross section of the pore, and not only the pore walls (see FIG. 18C for a diagrammatic representation of a polymer cross-linked so as to extend into and/or across the nanopore; note that the polymer is in a mesh-like state so as to partially block, but not to completely block the nanopore; the mesh will generally be at the most distal portion of the interior of the nanopore). The potential sensitivity of such a system has been demonstrated with covalently attached, pH-responsive "polymer brushes," which changed rectification behavior of thin-film nanopores as a result of protonation of phosphate groups on the polymer (Yameen, et al. Chem. Commun. 46, 1908-1910 (2010). Such a system, however, relies on a charged analyte (hydronium ion) to elicit a response. No previous nanopore sensors are known in which binding of a neutral analyte causes a change in charge state of the nanopore environment, influencing current rectification.

Methods

Reagents and Solutions:

All stock solutions were prepared in Milli-Q ultrapure water. Buffer solutions were prepared from potassium chloride (Baker), sodium phosphate (dibasic), sodium carbonate, and sodium bicarbonate (Sigma), and adjusted with either HCl (1 M) or KOH (0.1 M). Alizarin red sulfonate (ARS), 8-Hydroxypyrene-1,3,6-trisulfonic acid, trisodium salt (HPTS), esculetin, L-glucose, and L-fructose were purchased from Sigma. All buffer solutions used for analysis contained 10 mM buffer and 100 mM potassium chloride unless otherwise indicated.

Synthesis of Polymer PVP-BA:

Poly(4-vinylpyridine) (MW 60,000) was purchased from Sigma and used as received. The synthesis of o-bromomethylphenylboronic acid was carried out using an established procedure. To a 10 mL round bottom flask containing a magnetic stir bar were added poly(4-vinylpyridine) (0.100 g, 0.00167 mmols) and m-bromomethyl phenylboronic acid (0.206 g, 0.954 mmols). Then N,N-dimethylformamide (2 mL) and methanol (2 mL) were added to dissolve the reagents. The mixture stirred 23 hours, then was added dropwise to a 50 mL beaker containing dichloromethane (10 mL) to precipitate the product. The beaker was placed in an ice bath to allow the complete precipitation of the product. The solution was then poured into a two-piece fritted filter with removable top and vacuum-filtered under inert conditions using argon gas. The product was washed with 3×15 mL portions of dichloromethane, then left in a vacuum dessicator to dry overnight. Product isolated was 0.257 g (90% yield). $^1$H-NMR showed 82% alkylation of the polymer (data not shown).

Measuring Carbohydrate Response with Fluorimetry:

A probe solution was prepared consisting of PVP-BA (0.006% w/v) and HPTS ($1.5 \times 10^{-6}$ M) in methanol/water (1:1). An aliquot of 1 mL of the probe solution was added to a cuvette followed by 1 mL of carbonate buffer (20 mM carbonate, 100 mM potassium chloride, pH 9.5). The fluorescence was read using a filter pair of 460 nm (excitation) and 515-570 nm (emission). Aliquots of saccharide solutions (500 mM in water) were added, the solution was mixed by slowly pipetting for 1 min, and the fluorescence was measured after each addition. The total volume added did not exceed 20 microliters (1% of total volume). The fluorescent signal was converted to fluorescence increase ($F/F_0$). The averaged signal from multiple blank values was taken as the baseline fluorescence, F. Dividing each signal by this blank value gave the fluorescence increase.

Current Measurement with Quartz Nanopipette Electrodes:

Nanopipettes were fabricated using a P-2000 laser puller (Sutter Instrument Co.) from quartz capillaries with filaments, with an outer diameter of 1.0 mm and an inner diameter of 0.70 mm (QF100-70-5; Sutter Instrument Co.). Parameters used were: Heat 625, Filament 4, Velocity 60, Delay 170, and Pull 180. To measure ion current, a two electrode setup was used. The nanopipette was backfilled with buffer solution (phosphate/KCl, pH 7) and an Ag/AgCl electrode inserted. Another Ag/AgCl electrode was placed in 0.3 mL bulk solution acting as auxiliary/reference electrode. Both electrodes were connected to an Axopatch 700B amplifier with the DigiData 1322A digitizer (Molecular Devices), and a PC equipped with pClamp 10 software (Molecular Devices). To ensure complete wetting of the nanopipette electrodes, nanopipette tips were immersed in N,N-dimethylformamide for 5-10 seconds after being backfilled with buffer. Positive potential refers to anodic potential applied to the electrode in the barrel of the nanopipette relative to the counter electrode. Experiments were carried out at 24° C.

Embedding PVPBA in Nanopipettes:

Nanopipette barrels were filled with phosphate buffer (pH 7) and immersed in carbonate buffer (pH 9.5) containing the counter electrode. After verifying the nanopipettes displayed negative current rectification, they were briefly immersed in a methanol solution containing 0.03% (w/v) polymer, then returned to the carbonate solution. Successful immobilization of the polymer resulted in complete reversal of current rectification.

Measuring Carbohydrate Response with Polymer-Modified Nanopipettes:

Modified nanopipettes were analyzed in 0.30 mL of a carbonate buffer solution (pH 9.5) containing the counter electrode. To the solution were added aliquots of concentrated analyte solutions in pure water. The total volume added did not exceed 15 μL, in order to limit the change in volume to 5%. To measure response in real time, the current was analyzed using a sinusoidal potential at frequency of 0.5 Hz from −500 to +500 mV. After the signal had stabilized following addition of an aliquot, the current was analyzed by sweeping the voltage from −500 to +500 mV at a rate of 0.5 mV/ms. Each measurement consisted of 5 sweeps.

Electrochemical Data Analysis:

Ion current measurements recorded with pClamp software (sampling frequency 1000 Hz for voltage sweeps, 200 Hz for sinusoidal function) were imported to OriginPro 8.5 (Origin Labs) for analysis and graphing. To generate I-V curves for each data point, 5 voltage sweeps from −800 to +800 mV s$^{-1}$ at a scan rate of 500 mV s$^{-1}$ were averaged and the standard deviation calculated for each point. To generate binding isotherms, the current at a fixed potential was plotted as a function of analyte concentration.

Chemical Properties of the Functional Polyelectrolyte

To make a cationic, carbohydrate-responsive polymer, m-bromomethyl phenylboronic acid was used to alkylate a commercially available poly(4-vinylpyridine) (PVP) of molecular weight 60,000. The product, PVP-BA, precipitated from the reaction mixture in N,N-dimethylformamide and methanol. It is weakly soluble in methanol (up to 1% w/v), sparingly soluble in acidic methanol/water solutions, and practically insoluble in other aqueous and organic solvents. A benzylated version of the polymer (PVP-Bn), alkylated with benzyl bromide, showed much higher solubility. The alkylation efficiency of the polymers was determined by integration of $^1$H-NMR spectra. Polymer PVP-BA showed approximately 85% alkylation, while for PVP-Bn the alkylation efficiency was 90%. These values were used to estimate the molar mass of the polymers as 170,000 for PVP-BA and 150,000 for PVP-Bn. Polyelectrolytes such as poly(vinylpyridine) can be analyzed by titration to characterize protein uptake and apparent $pK_a$.[32]

Figure 20:
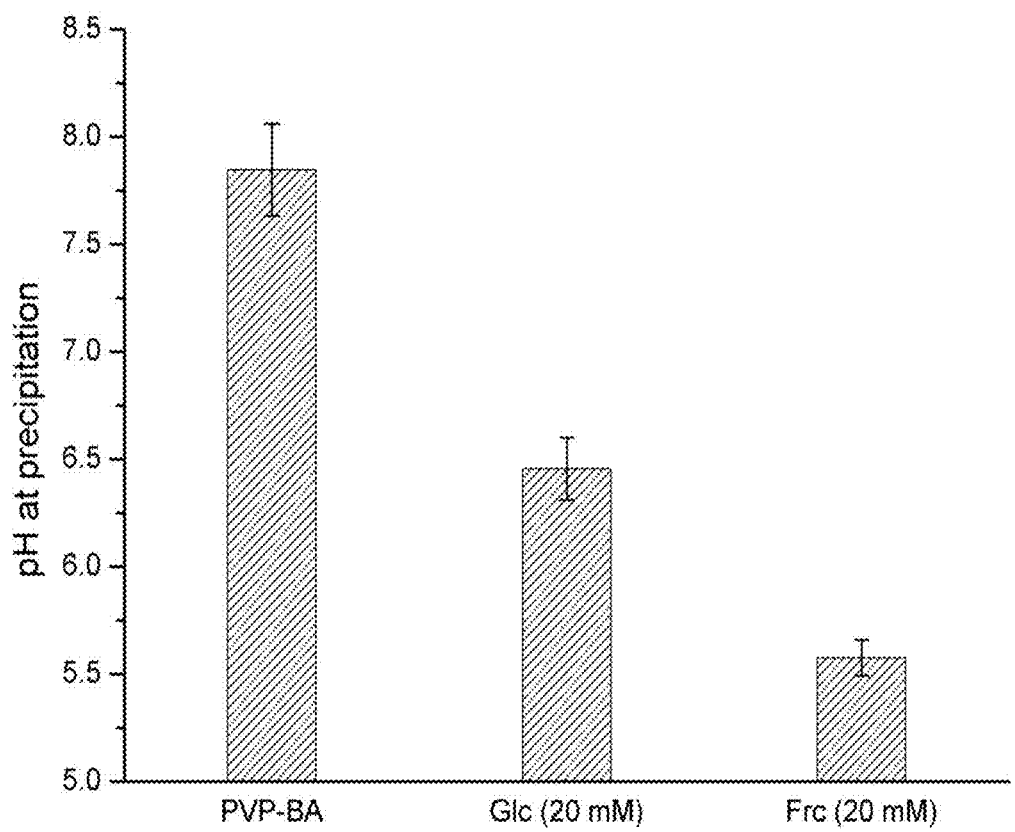
FIG. 20 is a bar graph showing the precipitation of PVP-BA in the presence of monosaccharides. A stifling solution of PVP-BA in methanol/water at pH 2 was titrated with sodium hydroxide until precipitation occurred. The error bars show standard deviation from three separate experiments.

To evaluate the pH-dependence of polymer PVP-BA, a solution of 1% w/v in methanol/water was acidified to pH 2. When titrated with hydroxide, the polymer quickly precipitated at approximately pH 8. This precipitation point was highly reproducible, and is consistent with the $pK_a$ of phenylboronic acid in solution. At that point, conversion of the boronic acid to boronate will effectively neutralize the charge from pyridinium groups, forming a zwitterionic polymer that is much less polar. This precipitation point is modulated in the presence of 20 mM monosaccharides (see pH at precipitation data, FIG. 20), which are known to lower the $pK_a$ of boronic acid by as much as 2 pH units. Compared to the precipitation of PVP-BA at pH 7.8±0.2, glucose causes the precipitation to occur at pH 6.5±0.1, and fructose causes precipitation at pH 5.58±0.08. Fructose is known to have a high affinity with most boronic acid receptors. This work shows that both glucose and fructose bind to the PVP-BA used. This method can be used to determine whether various polyelectrolytes can be used as coatings on the nanopipette, and to adjust the pH responsiveness of the polymers, e.g. by adding negatively charged groups or altering the positions of the negatively charged groups.

Figure 21:
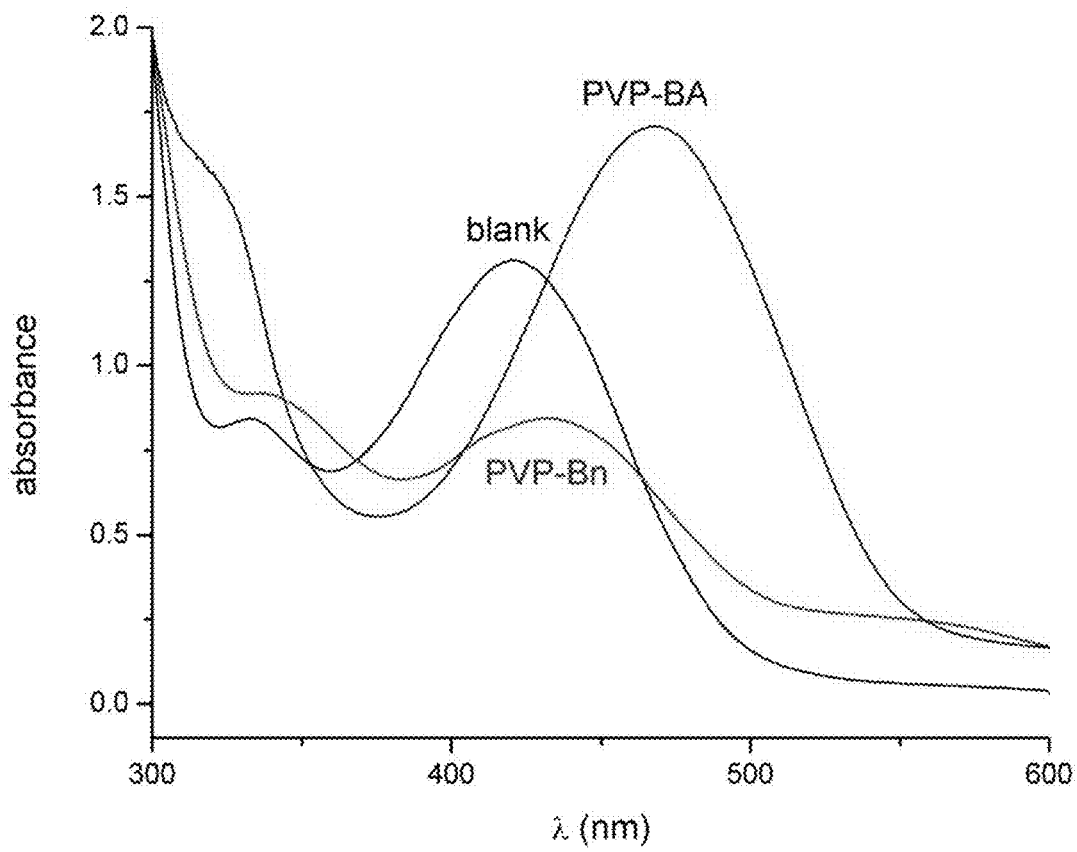
FIG. 21 is a graph showing the change in absorbance of ARS in the presence of polymers PVP-BA and PVP-Bn at 1 micromolar polymer concentration. The dye solution is 0.25 mM in 1:1 methanol/water.

To better characterize the interaction of the cationic polymer with carbohydrates, three colorimetric dyes were selected that can each interact with the polymers PVP-BA and PVP-Bn. These dyes act as surrogates for glucose sensing, were commercially available, and have published structures. Alizarin red sulfonate (ARS), contains both a catechol and a negative charge, esculetin, which contains only a catechol, and 8-Hydroxypyrene-1,3,6-trisulfonic acid, trisodium salt (HPTS), a dye with three negative charges. Solutions of each dye were titrated with polymer, and the absorbance spectra recorded. A representative absorbance spectrum is shown in FIG. 21 for ARS dye together with either PVP-BA or PVP-Bn. In the presence of PVP-Bn, which does not contain boronic acids, the absorbance maximum at 420 nm decreases and is slightly red-shifted to 432 nm. When PVP-BA is added to the dye, the maximum absorbance increases and is shifted to 467 nm. These two distinct phenomena show an interaction due to both boronic acid binding and electrostatic interactions. Also, the ARS bound to the BA polymer, but not the Bn polymer.

By measuring the difference in absorbance at $\lambda_{max}$, a curve was obtained showing ΔA as a function of polymer concentration. The sensitivity of each dye to the polymers was measured using the slope of the linear portion of curve, summarized in Table 1. For PVP-BA, the boronic acid-appended polycation, the affinity for ARS was double that of HPTS, showing a synergistic effect of both electrostatic attraction and bond formation. In contrast, PVP-Bn showed stronger affinity for HPTS compared to ARS, consistent with an all-electrostatic mechanism. Significantly, the affinity for esculetin is one order of magnitude lower for PVP-Bn than PVP-BA. This shows that without the presence of the boronic acid, there is little interaction between the polycation and uncharged catechol. While plotting ΔA vs. polymer concentration produced a smooth curve for all dyes tested, none showed a good fit to a standard binding isotherm. This is likely due to the complex nature of the polymer, which has multiple binding sites (approximately 500 per polymer chain) and may undergo aggregation in the presence of the dyes.

TABLE 1

Relative affinity of polymers for colorimetric dyes.

| | Sensitivity (μM$^{-1}$) | |
| --- | --- | --- |
| | PVP-BA | PVP-Bn |
| ARS | 2.09 ± 0.04 | 0.70 ± 0.02 |
| Esculetin | 1.53 ± 0.05 | 0.11 ± 01 |
| HPTS | 1.02 ± 0.05 | 1.53 ± 0.02 |

Note: Dyes were titrated with solutions of the polymers, and the slope was calculated as change in $\lambda_{max}$ as a function of polymer concentration.

Nanopipettes Embedded with Functional Polymer

To form a nanochannel functionalized with the boronic acid-containing polycation PVP-BA, quartz nanopipettes (pore diameter 20-40 nm) filled with phosphate buffer were used. In this medium, the polymer is insoluble. Before addition of the polymer, these show negatively rectified ion current at pH 7. That is, the IV plot shows higher current at negative voltage. To functionalize the nanochannel with the polymer, nanopipettes were briefly immersed in a methanol solution containing the polymer at 0.3% concentration (w/v). On returning the nanopipette tip to neutral buffer solution the current rectification is reversed, showing non-linear conductance that is higher at positive potentials. The PVP-BA pipette showed greater ion current at +voltage, and very little current at negative potential.

The inverted current rectification is evidence that the polymer penetrates the pore of the nanopipette, where the impedance of the system is highest. Several such polymer-modified nanochannels were produced in which the positive rectification was stable over a matter of hours. No polymer was visible on the outside of the nanopipette. Presumably, the modified ion current arises from polymer that is embedded in the nanochannel, held in place by both electrostatic attraction to the negatively charged quartz and limited solubility in the buffer. Imaging of the polymer within the nanochannel is not practical, but to approximate the system a micropipette was subjected to similar treatment. A micropipette of 20 micrometer pore diameter was filled with phosphate buffer containing 1 mM ARS for visualization of the polymer. Immersion in a methanol solution of the polymer produces a violet color at the very tip of the micropipette. Even after 20 minutes, very little of the polymer diffused up into the wider opening of the pipette tip.

The pH sensitivity of modified nanopipette electrodes is considerably greater than quartz nanopipettes. The negative rectification of a bare quartz nanopipette shows only a slight decrease at pH 3, corresponding to protonation of silanoxy groups. In contrast, a nanopipette with embedded PVP-BA shows virtually no conductance at negative potentials from pH 8 to pH 3 (data not shown). The conductance at positive potentials increases with decreasing pH, showing the most change between pH 5 and pH 3. The electrochemical behavior of the nanochannel/polymer material is not predicted from the properties of the polymer in solution, which undergoes the biggest change in protonation state between pH 7 and 8.

Figure 22:
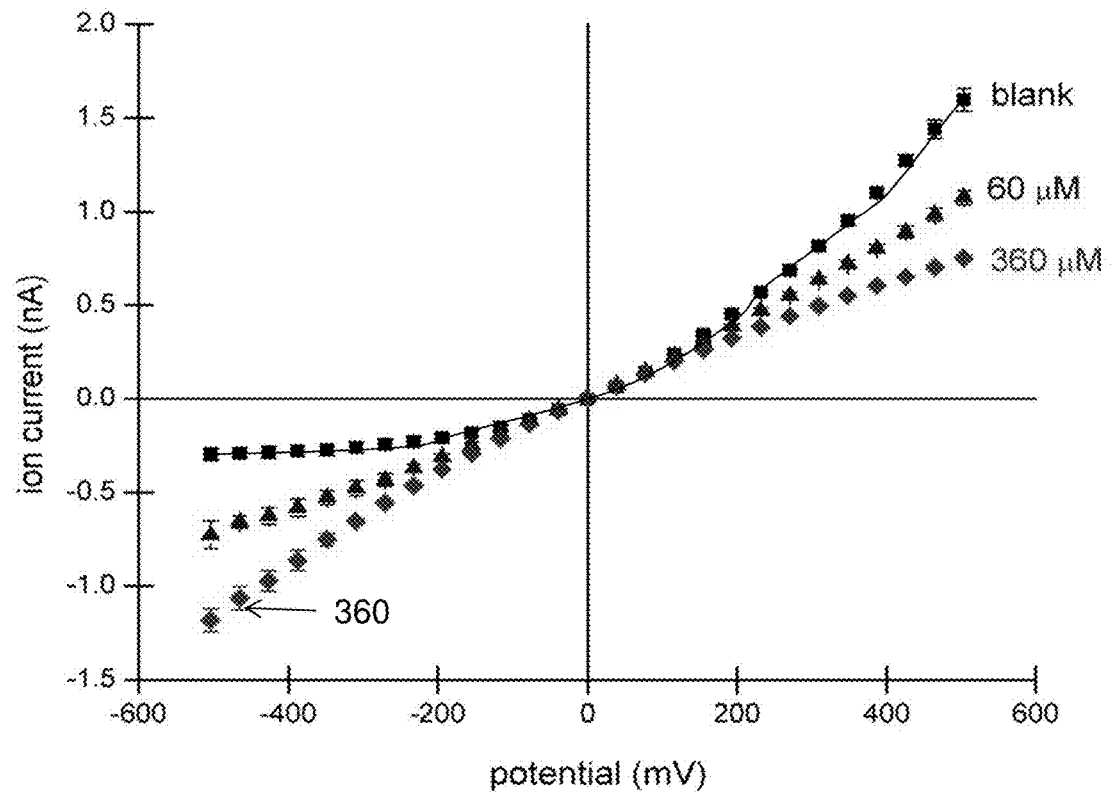
FIG. 22 is an IV plot showing the modulation of ion permeability in the presence of ARS. A nanopipette embedded with the polymer PVP-BA was immersed in pH 9.5 carbonate buffer containing either 0, 60, or 360 µM ARS. Error bars shown standard deviation from repeated voltage ramps (N=5).

The anionic catechol ARS showed the highest affinity for polymer PVP-BA in solution among the dyes tested. To test modulation of ion permselectivity with this dye, polymer-modified nanopipettes were immersed in carbonate buffer of pH 9.5. Under these basic conditions, the formation of anionic boronate esters is ensured.[34] As shown in FIG. 22, as little as 60 µM ARS is sufficient to negate all positive rectification in a modified nanochannel. With 360 µM ARS, the current is negatively rectified. Referring to FIG. 22, the arrow at 360 shows the increased negative current at a negative voltage. In this example, a negative current of about −1 nA is observed at −500 mV, while +500 mV resulted in about +0.6 nA. The example also shows how the blank, 60 µM and 360 µM concentrations of ARS can be distinguished. Because the ion current rectification becomes reversed, addition of the dye does not appear to cause blockage of the nanopore, or nanochannel. Rather, the ion permeability of the channel is reversed based on reversal of electrostatic charge within the matrix.

At low concentrations of ARS (<0.1 mM), the modulation of ion current rectification is completely reversible, requiring no washing media. Higher concentrations caused the system to become permanently negatively rectified. This may be due to strong interactions between the polymer and the dye, especially if the dye penetrates deep into the polymer matrix where it is prevented from diffusing into the bulk solution.

Figure 23:
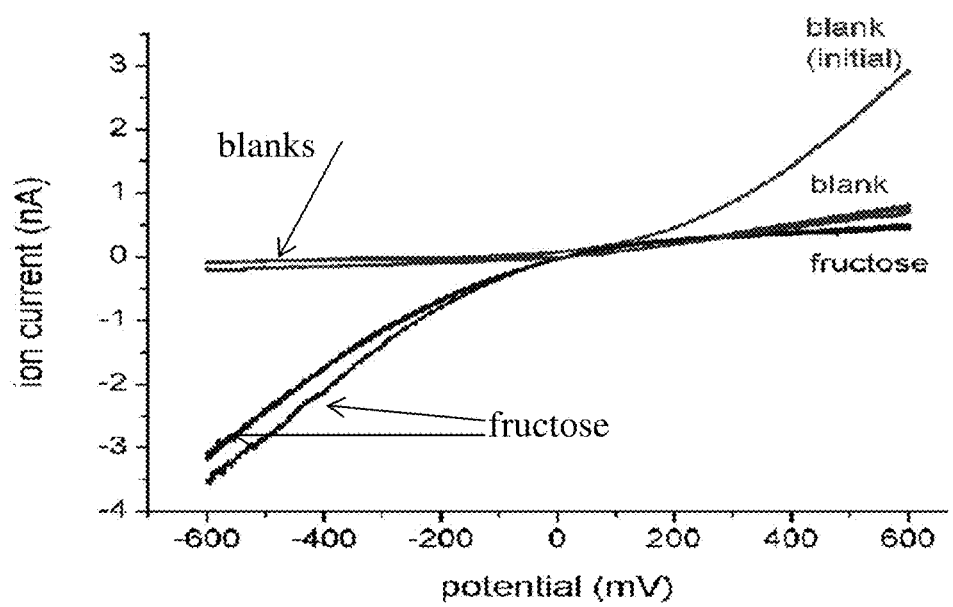
FIG. 23 is a graph showing the inversion of ion current rectification with fructose. Current-voltage curves for a PVP-BA-embedded nanochannel at pH 9.5 without and with 10 mM fructose.
Figure 24:
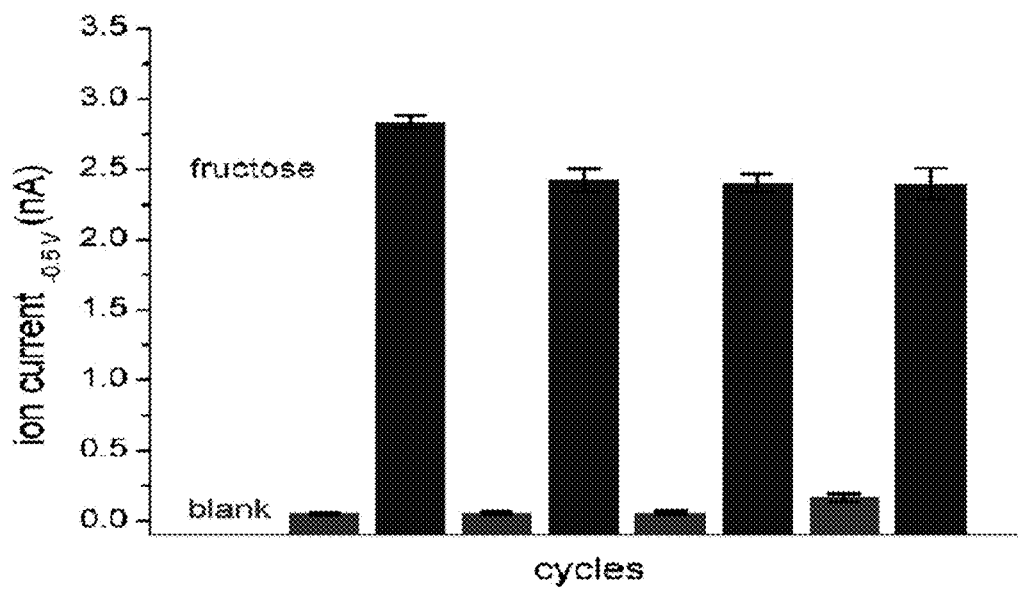
FIG. 24 is a graph that shows sequential cycles of ion current modulation measured at −0.5 V with and without fructose. Error bars show the standard deviation from repeated voltage scans (N=5). Equilibration time was 5 minutes at each condition
Figure 25:
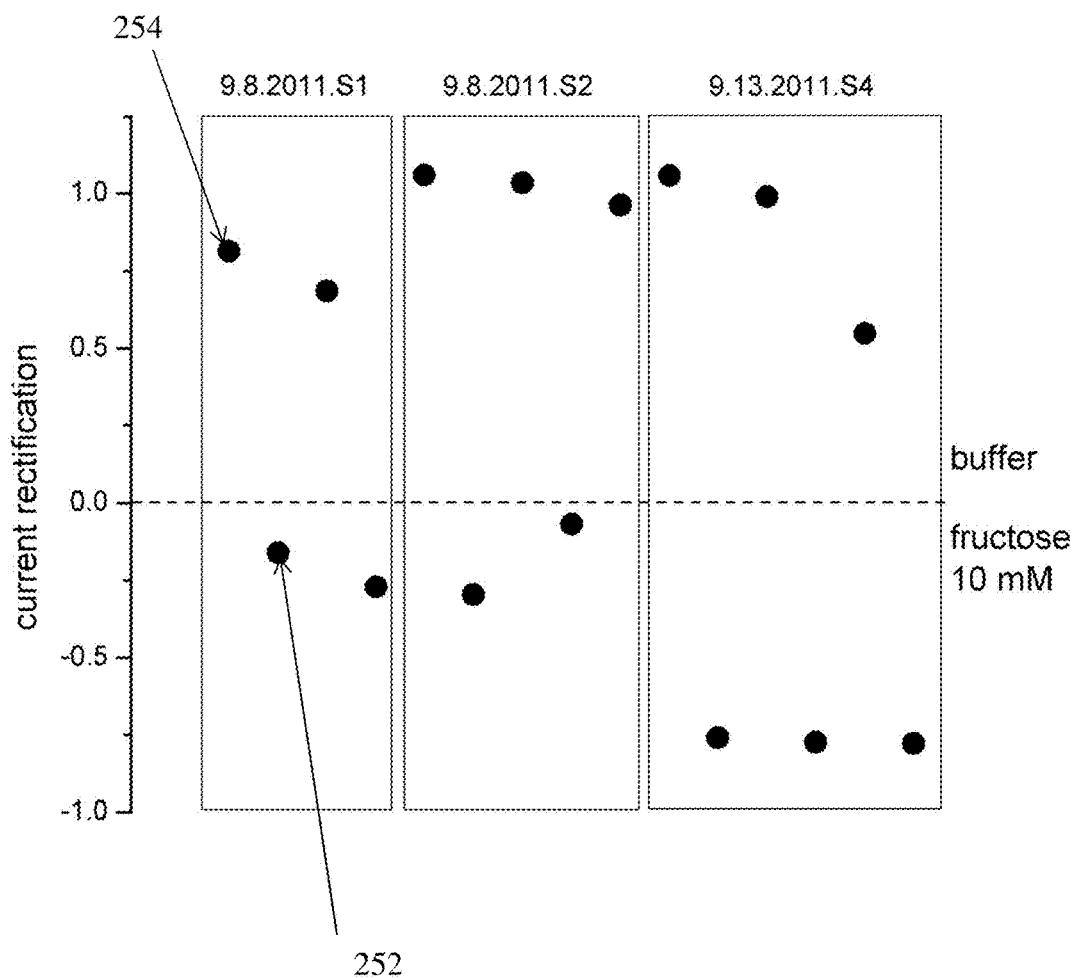
FIG. 25 is a graphic showing the reversible ion current rectification values for three separate nanopipette sensors. Sensors were immersed in carbonate buffer (pH 9.5) with or without fructose (10 mM). Positive rectification for sensor S1 in buffer is shown at 254. Negative rectification of sensor S1 in fructose is shown at 252.

The reversal of ion current rectification in the modified nanochannel shown with ARS may be due to both the charge of the dye as well as a $pK_a$ shift in the boronic acid-containing matrix. For neutral carbohydrates, a change in rectification must be attributed to boronic acid/boronate equillibria in the nanochannel. The addition of fructose (10 mM) to a polymer-embedded nanochannel resulted in rapid inversion of current rectification from positive to negative (FIG. 23-24). The curves in FIG. 23 show that there is almost no rectification in the blank nanopipettes, while the presence of fructose at 10 mM resulted in an IV curve exhibiting negative rectification (i.e. higher current at negative voltage). FIG. 24 shows the reversibility of the binding, in that the response time for complete inversion of current rectification is 3 to 5 minutes, both on exposure to fructose and on returning the nanopipette tip to pure buffer. Interestingly, only a portion of the initial positively rectified I-V curve is restored after exposure to fructose. As shown in FIG. 23, the conductance at negative potentials undergoes complete and reproducible switching in repeated cycles of fructose exposure. This is not necessarily the case for positive potentials. As shown in FIG. 23, the initial signal for a PVP-BA modified nanopipette is highly open at positive potentials up to 600 mV. This open state does not become completely restored after exposure to fructose. This indicates some conditioning of the matrix in the nanochannel as a result of carbohydrate binding. While the magnitude of current rectification differed among different polymer-embedded nanochannels, the inversion of rectification in the presence of fructose was complete and reversible for several systems tested (FIG. 25). Exemplary spots 254 and 255 show positive and negative rectification, respectively, in different experiments.

Because of the complete reversal of current response at negative potentials, a current at fixed negative potential can be used to show fructose modulated gating between an open and closed state. As shown in FIG. 24, the current at −500 mV is completely reversible with several cycles of fructose exposure. Significantly, there are no washing conditions required to restore the signal. It should also be noted from the smoothness of the I-V curves that the polymer matrix does not appear to be influenced by the electric field. Rather, it is only the presence of a neutral carbohydrate that modulates ion permeability in the nanochannel.

Figure 27:
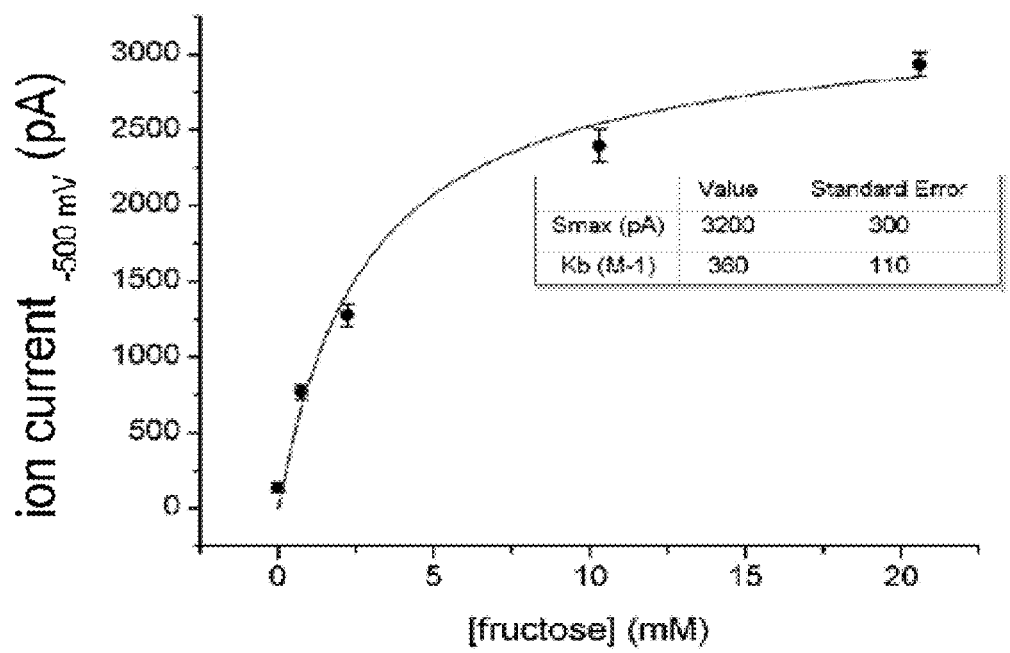
FIG. 27 is a graph of data as shown in FIG. 26 using an electrochemical method using a modified conical nanochannel.

The response of the modified nanochannel to fructose, as with ARS, is concentration-dependent (FIGS. 26-27). By plotting the current at potential of −500 mV as a function of fructose concentration, a binding affinity can be determined for a given nanochannel, given by the following equation:

$$S=(1+S_{max}K_b[A])/(1+K_b[A])$$

This model uses S as the signal, in this case ion current, $S_{max}$ as the calculated signal upon saturation with analyte, [A] as the analyte concentration, and $K_b$ as the binding constant in units of $M^{-1}$. The binding constant determined from fitting of the curve is 360±110 $M^{-1}$ for the nanochannel shown, which is consistent with binding constants measured using mono-phenylboronic acids in solution. These affinities can vary widely, but are generally within the range of 100 to 5000 $M^{-1}$. To compare the response of the nanochannel-confined polymer to the solution phase polymer, a fluorescence-based assay was carried out which, like the nanochannel electrode, is modulated by electrostatic charge. Using the dye HPTS, an allosteric indicator-displacement assay (AIDA) was used to measure fructose response. In solution, HPTS forms a ground-state complex with PVP-BA polymer, quenching fluorescence. The two components are attracted electrostatically; the cationic polyelectrolyte to the anionic dye. At pH 9.5, the addition of fructose causes boronic acid groups on the polymer to become anionic boronates, neutralizing the overall positive charge on the polymer and displacing the fluorescent dye. With this system, an apparent binding constant was determined as 3200±400 $M^{-1}$ for fructose (FIG. 26). This affinity is an order of magnitude greater than that measured with the polymer in a conical nanochannel, but still well within reported values for boronic acid-fructose binding. While the environments for the polymer are very different for both systems, in both cases it is a modulation in polymer charge that gives a signal. The ability to quickly engineer a stimulus-responsive nanofluidic diode using a well-characterized receptor matrix offers a new strategy to control ion permeability in nanopores.

Thus the data in FIGS. 25 and 26 show that the fluorescence values obtained in an accepted assay are comparable to the ion current values obtained at varying concentrations of fructose at a set negative voltage, and that the present electrochemical method has a higher dynamic range than the fluorescence method.

Sensors comprising nanopipettes embedded with PVP-BA polymer were also shown to respond to glucose with an increase in negative rectification at pH 9.5. A sensor showing negative rectification ratio of 1.42 in buffer was exposed to 20 mM glucose, whereupon the negative current increased resulting in negative rectification ratio of 1.99. Negative current ratio is defined as the ratio of current at potential −500 mV to the current at potential +500 mV.

CONCLUSION

The above specific description is meant to exemplify and illustrate the invention and should not be seen as limiting the scope of the invention, which is defined by the literal and equivalent scope of the appended claims. Any patents or publications mentioned in this specification are intended to convey details of methods and materials useful in carrying out certain aspects of the invention which may not be explicitly set out but which would be understood by workers in the field. Such patents or publications are hereby incorporated by reference to the same extent as if each was specifically and individually incorporated by reference and contained herein, as needed for the purpose of describing and enabling the method or material referred to.

What is claimed is:

1. A method for creating an ionic compound from two different ions in solution, comprising:
   (a) providing at least one first ion species having a charge in a first solution inside of a nanopipette, said nanopipette having a nanopore between an interior of the nanopipette and an exterior solution;
   (b) providing a second ion species in the exterior solution, wherein the first solution and the exterior solution have the same polarity; and
   (c) applying, to the first ion species having a charge in the first solution inside of the nanopipette, a voltage across the nanopore of opposite charge from the charge on the first ion species, said voltage sufficient to cause migration of said first ion species to the nanopore to react with said second ion species to form an ionic compound,
   wherein the nanopipette has a capillary portion defining an interior bore of the nanopipette, wherein the interior bore is elongated and tapers to a tip with the nanopore positioned at the tip of the nanopipette, wherein the nanopore has an inner diameter in the range of 37 nm-82 nm and the outer diameter of the nanopore is less than 1 µm,
   wherein the first solution is different from the exterior solution and prior to step (c), the first and second ion species are isolated from each other in the first and exterior solutions, respectively.

2. The method of claim 1 further comprising the step of measuring ionic current through the nanopore and detecting a change in current indicative of formation of the ionic compound.

3. The method of claim 1 wherein said change in current indicative of formation of the ionic compound is an oscillation.

4. The method of claim 1 wherein the ionic compound is insoluble.

5. The method of claim 1 wherein either the first ion species or the second ion species is a metal cation reacting with an anion to form the ionic compound.

6. The method of claim 5 wherein the metal cation is a transition metal cation.

7. The method of claim 5 wherein the metal cation is selected from the group consisting of: $Mg^{2+}$, $Ca^{2+}$, $Mn^{2+}$, $Zn^{2+}$, $Cu^{2+}$, $Fe^{2+}$, $Fe^{3+}$, $Cr^{3+}$, $Cr^{6+}$, $Cd^{2+}$, $Mo^{2+}$, $Co^{3+}$, $Co^{2+}$, $Hg^{2+}$, $Ni^{2+}$, $Al^{3+}$, $Al^{2+}$, $Ar^{3+}$, $Ar^{3-}$, and $Pb^{2+}$.

8. The method of claim 1 wherein the first ion species or the second ion species is an anion selected from the group consisting of: phosphate, chloride, sulfate, monophosphate, pyrophosphate, metaphosphate, tripolyphosphate, tetrametaphosphate, and orthophosphate.

9. The method of claim 1 wherein the first ion species or the second ion species is an anion, wherein the anion is an organic carboxylic acid anion selected from the group consisting of: gluconate, tartrate, fumarate, maleate, malonate, malate, lactate, citrate, EDTA, citraconate, citramalate, stearate, oleate, laurate, octoate, ascorbate, picolinate, and orotate.

10. The method of claim 1 wherein either the first ion species or the second ion species is a protein.

11. The method of claim 1 further comprising the step of reversing said voltage after a precipitate has formed.

12. The method of claim 1 further comprising the step of detecting the formation of an ionic compound created.

13. The method of claim 1, wherein the first solution and the exterior solution are aqueous solutions.

14. The method of claim 1, wherein the nanopore has an inner diameter is in the range of 40 nm-60 nm.

15. The method of claim 1, wherein the first ion species is negatively charged and the second ion species is positively charged and wherein the voltage is a negative voltage.

16. A method for creating an ionic compound from two different ions in solution, comprising:
   (a) providing at least one first ion species having a charge in a first solution inside of a nanopipette, with a nanopore between an interior of the nanopipette and an exterior solution,
   wherein the nanopore has an inner diameter in the range of 37 nm-82 nm and the outer diameter of the nanopore is less than 1 µm;
   (b) providing a second ion species in the exterior solution; and
   (c) applying to the first ion species, having a charge in the first solution inside of the nanopipette, a voltage across the nanopore of opposite charge, said voltage sufficient to cause migration of the first ion species to the nanopore to react with the second ion species to form an ionic compound,
   wherein the first solution is different from the exterior solution and prior to step (c), the first and second ion species are isolated from each other in the first and exterior solutions, respectively,
   wherein the nanopipette has a capillary portion defining an interior bore of the nanopipette leading to the nanopore and a coating on an interior surface of the nanopore, the coating comprising:
(i) a polyelectrolyte layer bound directly to the interior surface; and
(ii) a binding molecule, linked to the polyelectrolyte layer, specific for binding an analyte which is selected from the group consisting of an ion or a small molecule having a molecular weight of less than 200 atomic mass units.

17. The method of claim 16, further comprising the step of measuring ionic current through the nanopore and detecting a change in current indicative of formation of the ionic compound.

18. The method of claim 16, wherein the binding molecule is a boronic acid or boronic esters.

19. The method of claim 16, wherein the polyelectrolyte layer is a polycation layer.

* * * * *

UNITED STATES PATENT AND TRADEMARK OFFICE
CERTIFICATE OF CORRECTION

| | |
|---|---|
| PATENT NO. | : 10,345,260 B2 |
| APPLICATION NO. | : 14/641064 |
| DATED | : July 9, 2019 |
| INVENTOR(S) | : Nader Pourmand et al. |

It is certified that error appears in the above-identified patent and that said Letters Patent is hereby corrected as shown below:

In the Specification

In Column 1, Lines 16-24, please replace the STATEMENT OF GOVERNMENTAL SUPPORT section with the following:
--This invention was made with government support under NCC9-165, NASA NNX08BA47A, and NASA NNX09AQ44A awarded by the National Aeronautics and Space Administration, and HG000205, and CA143803 awarded by the National Institutes of Health. The government has certain rights in the invention.--

Signed and Sealed this
Twenty-sixth Day of March, 2024

Katherine Kelly Vidal
*Director of the United States Patent and Trademark Office*